(12) United States Patent
Carron et al.

(10) Patent No.: US 10,251,580 B2
(45) Date of Patent: Apr. 9, 2019

(54) FLEXIBLE CIRCUIT FOR A SWALLOWABLE PILL

(71) Applicant: Rock West Medical Devices, LLC, San Juan Capistrano, CA (US)

(72) Inventors: Neal Jay Carron, Goleta, CA (US); Thomas Eugene Old, Santa Barbara, CA (US); Donald Gordon Pritchett, Santa Barbara, CA (US); John Christopher Baker, Santa Barbara, CA (US)

(73) Assignee: Rock West Medical Devices, LLC, Santa Barbara, CA (US)

( * ) Notice: Subject to any disclaimer, the term of this patent is extended or adjusted under 35 U.S.C. 154(b) by 0 days.

(21) Appl. No.: 15/885,211

(22) Filed: Jan. 31, 2018

(65) Prior Publication Data

US 2018/0214049 A1    Aug. 2, 2018

Related U.S. Application Data

(60) Provisional application No. 62/453,291, filed on Feb. 1, 2017.

(51) Int. Cl.
*A61B 5/07* (2006.01)
*A61B 1/04* (2006.01)
(Continued)

(52) U.S. Cl.
CPC .............. *A61B 5/073* (2013.01); *A61B 1/041* (2013.01); *A61B 5/062* (2013.01); *A61B 5/6861* (2013.01);
(Continued)

(58) Field of Classification Search
None
See application file for complete search history.

(56) References Cited

U.S. PATENT DOCUMENTS 7,511,733 B2 * 3/2009 Takizawa ........... A61B 1/00105
348/65
7,801,586 B2    9/2010 Muratayev et al.
(Continued)

OTHER PUBLICATIONS

Annex to Form PCT/ISA/206 Communication Relating to the Results of the Partial International Search dated May 8, 2018—PCT/US2018/016224.
(Continued)

*Primary Examiner* — Dimary S Lopez Cruz
(74) *Attorney, Agent, or Firm* — Knobbe, Martens, Olson & Bear, LLP

(57) ABSTRACT

This disclosure relates to a flexible circuit for insertion into a pill capsule. The flexible circuit has a first portion having an electrical contact to electrically connect with a battery, a second portion having an electrical contact to electrically connect with the battery, a first arm separating the first portion and second portion, a third portion comprising a first antenna, a second arm separating the first portion and third portion, a fourth portion comprising a second antenna, a third arm separating the first portion and fourth portion, a third arm separating the first portion and fourth portion, and a fifth portion comprising a third antenna. The first portion, second portion, and first arm form a first receptacle to receive a battery. The third portion, fourth portion, and fifth portion form a second receptacle to receive a cube ferrite core.

16 Claims, 16 Drawing Sheets

(51) Int. Cl.
*A61B 5/06* (2006.01)
*A61B 5/00* (2006.01)

(52) U.S. Cl.
CPC ... *A61B 2560/0214* (2013.01); *A61B 2562/12* (2013.01)

(56) References Cited

U.S. PATENT DOCUMENTS

| | | | | |
|---|---|---|---|---|
| 8,335,556 | B2* | 12/2012 | Uchiyama | A61B 1/00016 600/424 |
| 8,353,821 | B2* | 1/2013 | Segawa | A61B 1/0011 600/128 |
| 8,439,822 | B2 | 5/2013 | Shigemori et al. | |
| 8,591,403 | B2* | 11/2013 | Yoshida | A61B 1/00016 600/130 |
| 8,852,172 | B2 | 10/2014 | Dijksman et al. | |
| 9,186,040 | B2 | 11/2015 | Tanaka | |
| 9,270,025 | B2 | 2/2016 | Robertson et al. | |
| 2003/0181788 | A1* | 9/2003 | Yokoi | A61B 1/00087 600/160 |
| 2009/0131784 | A1 | 5/2009 | Betesh | |
| 2009/0292167 | A1* | 11/2009 | Kimoto | A61B 1/00016 600/109 |
| 2010/0326703 | A1 | 12/2010 | Gilad et al. | |
| 2011/0184235 | A1* | 7/2011 | Schostek | A61B 1/00158 600/109 |
| 2012/0296165 | A1* | 11/2012 | Segawa | A61B 1/041 600/109 |
| 2014/0149981 | A1 | 5/2014 | Luxenberg et al. | |
| 2014/0357949 | A1* | 12/2014 | Wilson | A61B 1/041 600/109 |
| 2015/0112189 | A1 | 4/2015 | Carron et al. | |

OTHER PUBLICATIONS

PCT Invitation to Pay Additional Search Fees—PCT/US2018/016224 dated May 8, 2018.

* cited by examiner

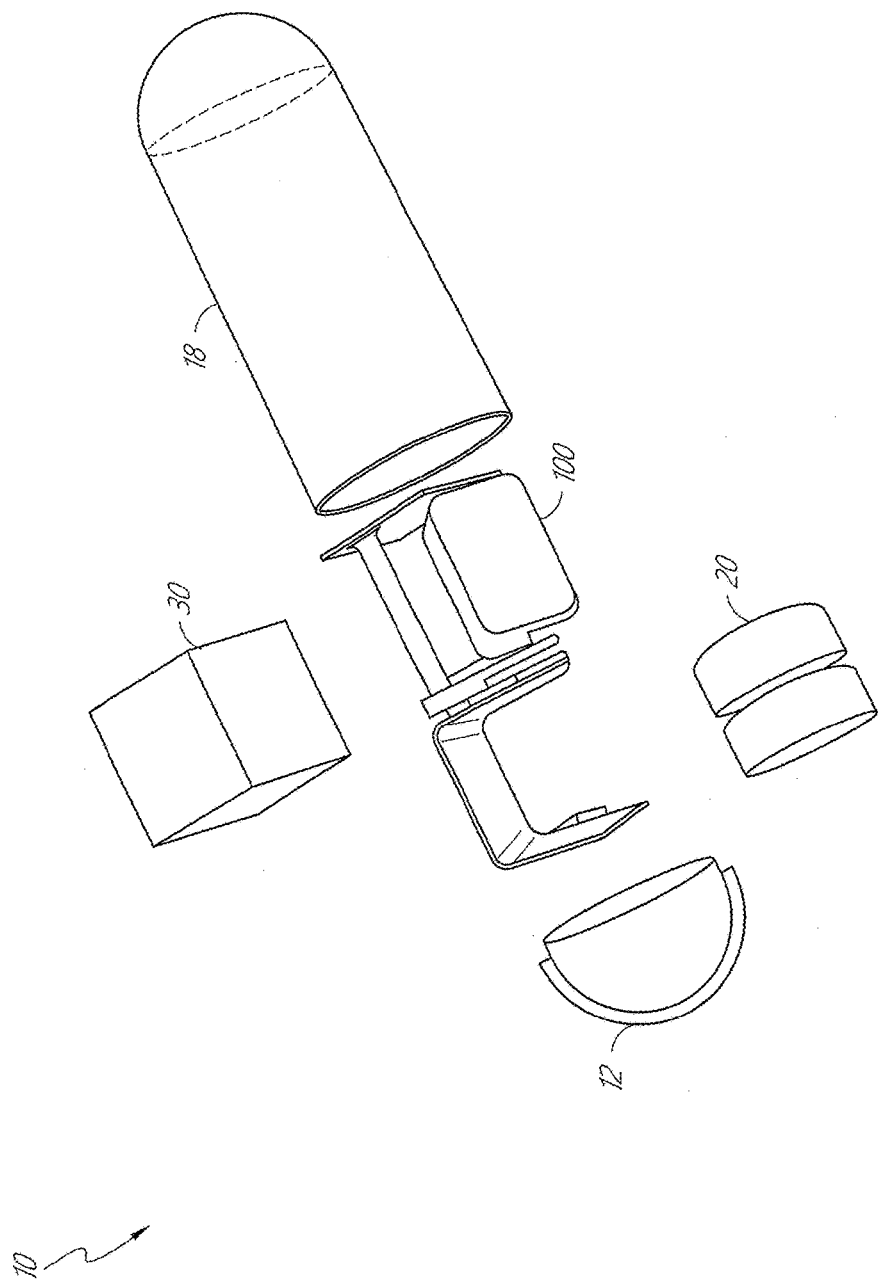

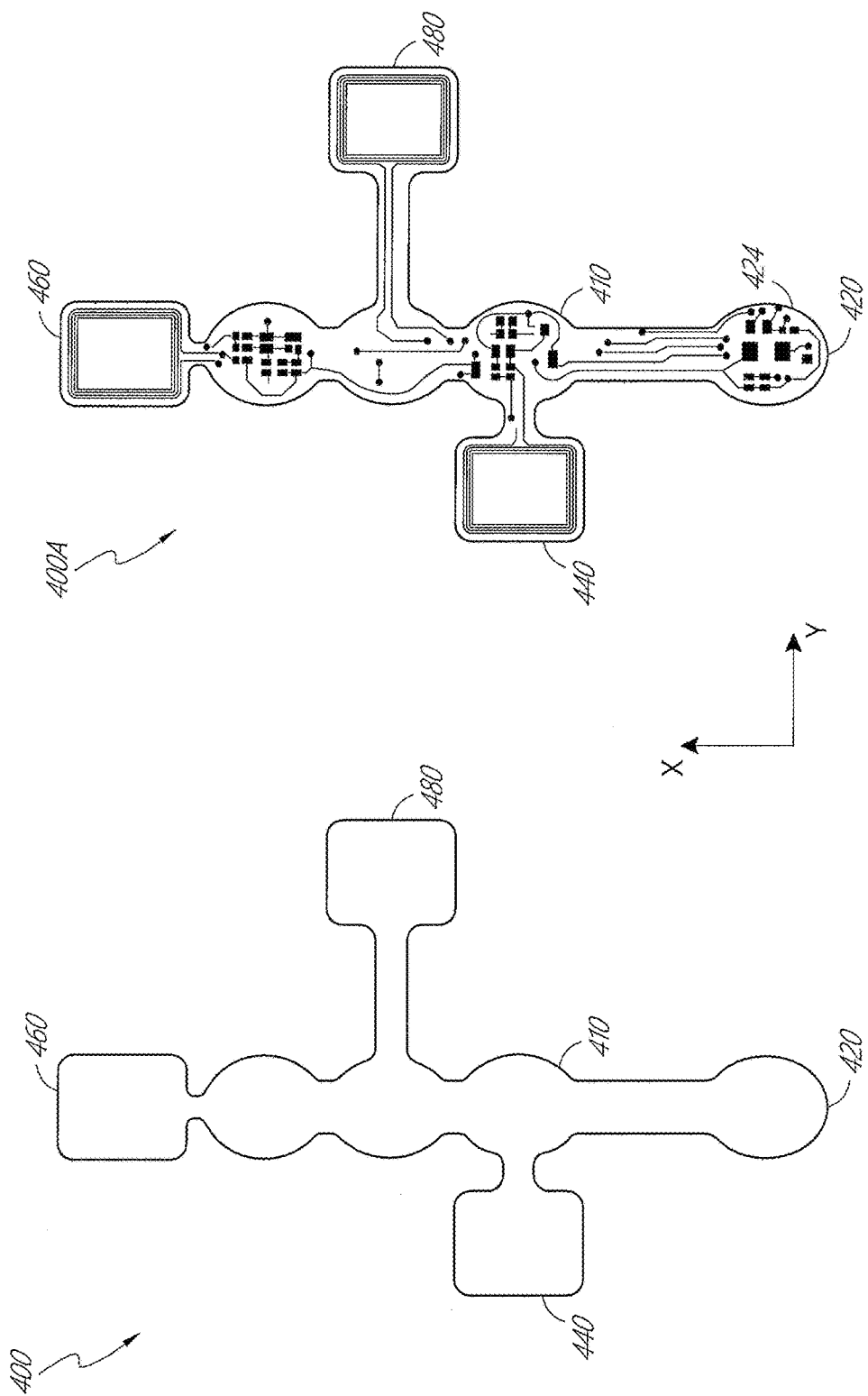

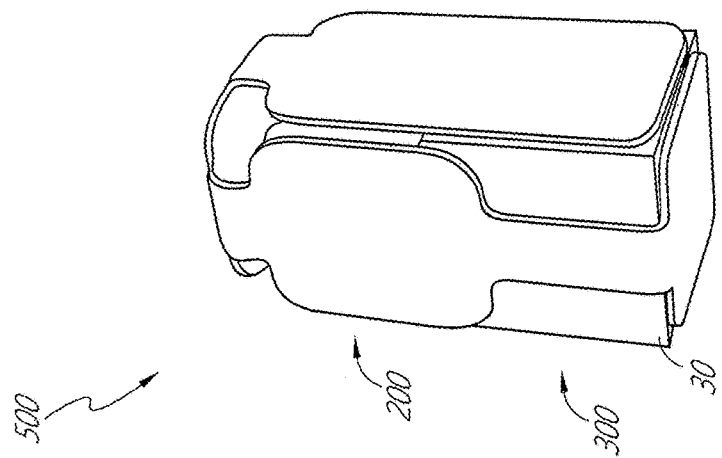
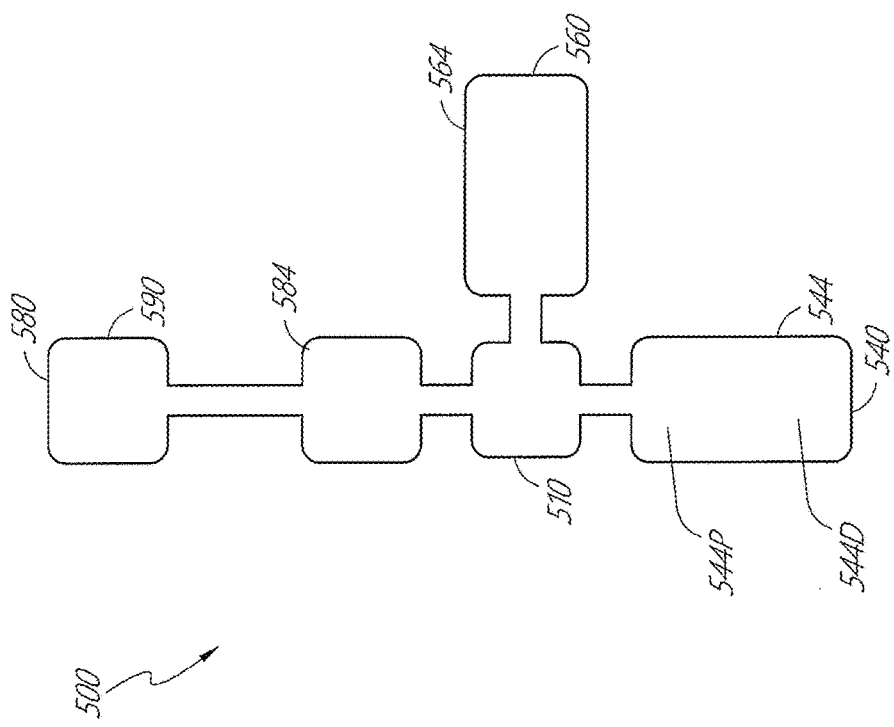
FIG. 5B
FIG. 5A

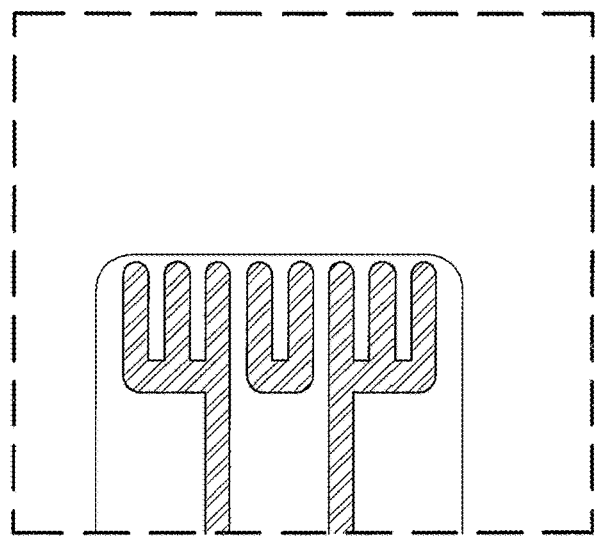
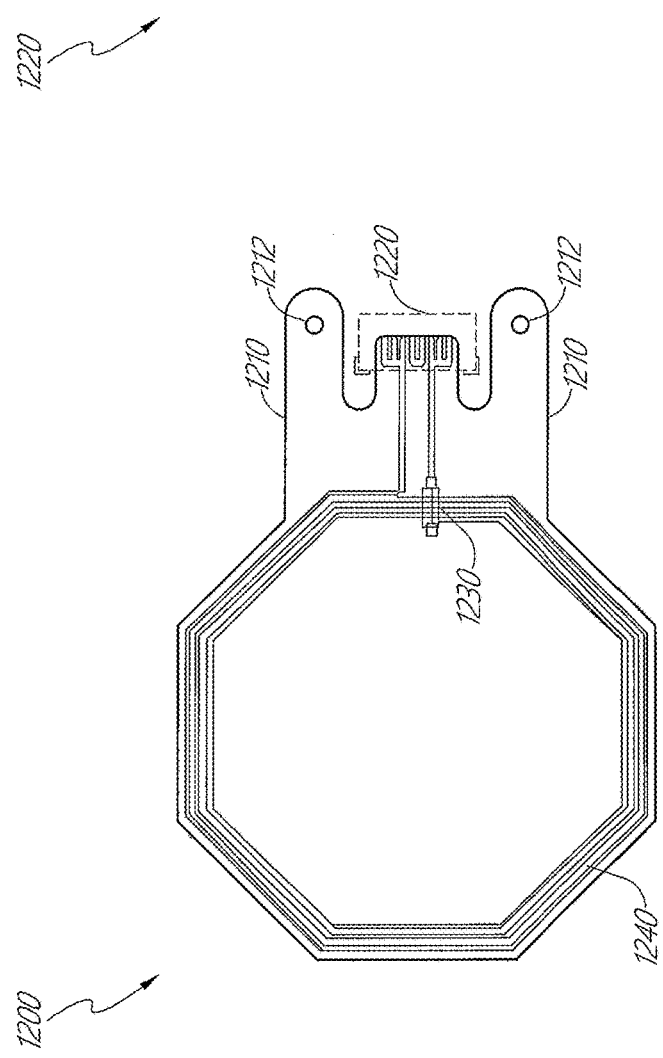
FIG. 12B
FIG. 12A

FLEXIBLE CIRCUIT FOR A SWALLOWABLE PILL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority under 35 U.S.C § 119(e) as a non-provisional of U.S. Provisional Application No. 62/453,291, filed Feb. 1, 2017, titled FLEXIBLE CIRCUIT FOR ANTENNA. This application is also related to U.S. application Ser. No. 14/520,219, filed Oct. 21, 2014, titled NEARLY ISOTROPIC DIPOLE ANTENNA SYSTEM, U.S. application Ser. No. 13/969,423, filed Aug. 16, 2013, titled SYSTEM AND METHODS FOR LOCATING RELATIVE POSITIONS OF MULTIPLE PATIENT ANTENNAS and application Ser. No. 14/667,563, filed Mar. 24, 2014, titled SYSTEM AND METHOD FOR TRIGGERING A RADIOFREQUENCY TRANSCEIVER IN THE HUMAN BODY. The disclosures of each of the foregoing applications are hereby incorporated by reference in their entirety.

BACKGROUND

Movement of food through the human digestive tract can be obstructed or slowed for a variety of reasons. Frequently, there may be little or no pain, yet the condition may result in death if the condition is not identified and treated quickly. Examples of these conditions include gastrointestinal (GI) motility abnormalities, directional flow issues, or intestinal blockages. Reasons for gastrointestinal dysmotility are numerous, including bowel strangulation, neuropathy, diverticulitis, paraplegia, diabetic gastroparesis, chemotherapy, mental conditions, and drug interaction. People of some or all ages can be affected, ranging from newborn babies to the elderly.

SUMMARY

For purposes of summarizing the disclosure, certain aspects, advantages and novel features have been described herein. It is to be understood that not necessarily all such advantages can be achieved in accordance with any particular embodiment disclosed herein. Thus, the embodiments disclosed herein can be embodied or carried out in a manner that achieves or optimizes one advantage or group of advantages as taught or suggested herein without necessarily achieving others.

In certain embodiments, a system for locating a pill swallowed by a patient can include body antennas, a modular electronics unit (MEU), and a pill. The pill can further include electronics, antennas, batteries, and packaging. The current system and methods are at first specifically addressed to a pill that can be ingested by a human or animal. In this application, the location of the pill can be determined by antennas or sensors worn on or placed near the patient's body. The current system facilitates the pill generation and field sensor measurement, and so enhances the ability to determine the pill location and to track the pill. The purpose is to follow the pill motion to determine if there are any gastro-intestinal motility abnormalities, directional flow issues, or intestinal blockages. Signals collected by the body antennas are sent to the modular electronics unit (MEU).

In certain embodiments, a flexible circuit that can be inserted into a pill capsule can include a first portion having an electrical contact to electrically connect with a first terminal of a battery, a second portion having an electrical contact to electrically connect with a second terminal of the battery, a first arm having a length separating the first portion and the second portion, a third portion having a first antenna, a second arm having a length separating the first portion and the third portion, a fourth portion having a second antenna, a third arm having a length separating the first portion and the fourth portion, and a fifth portion having a third antenna. Furthermore, the first portion, the second portion, and first arm can form a first receptacle in a folded configuration. The first receptacle can receive a battery. Furthermore, the third portion, the fourth portion, and the fifth portion can form a second receptacle in the folded configuration. The second receptacle can receive a cube ferrite core.

In some embodiments, the first portion can be positioned substantially parallel to the second portion and the fifth portion can be positioned substantially parallel to the first portion and the second portion in the folded configuration. Additionally, in certain embodiments, the third portion can be positioned substantially perpendicular to the fourth portion and the fifth portion can be positioned substantially perpendicular to the third portion and the fourth portion in the folded configuration.

The first antenna can transmit a first transmit signal in a first direction. The second antenna can transmit a second transmit signal in a second direction. The third antenna can transmit a third transmit signal in a third direction. Moreover, the first direction can be substantially perpendicular to the second direction and the third direction. Furthermore, the second direction can be substantially perpendicular to the first direction and third direction. The third direction can be substantially perpendicular to the first direction and the second direction.

In some embodiments, the first receptacle can have a volume proportional to the length of the first arm. The flexible circuit can further include the battery positioned in the first receptacle. The flexible circuit can further include the ferrite core positioned in the second receptacle. In certain embodiments, the flexible circuit can be integrated with a camera unit. In addition, the flexible circuit can also include a photodiode switch configured to detect optical radiation and activate operation of an electrical component in response to the detected optical radiation when the photodiode switch is positioned on.

In certain embodiments, a flexible circuit that can be inserted in a pill capsule can include a base, a first arm extending from the base, and a second arm extending from the base. Furthermore, the first arm can fold on a first side of the base and the second arm can fold on a second side opposite from the first side. Moreover, the base, the first arm, and the second arm can form a first recess and a second recess. In some embodiments, the first recess can house a battery and the second recess can house a ferrite core.

Additionally, the length of the first arm can be substantially equal to a sum of a length of the battery and a length of the ferrite core. The flexible circuit can include a first volume of the battery substantially equal to the first recess and a second volume of the ferrite core substantially equal to the second recess, thereby reducing empty space. Furthermore, the flexible circuit can include an empty volume defined by a difference between a volume formed by the base, the first arm, and the second arm and a volume of the battery and a volume of the ferrite core less than 20%. In some embodiments, the first arm can be positioned substantially parallel to the second arm. The flexible circuit can also include the battery positioned in the first receptacle. The flexible circuit can also include the ferrite core positioned in the second receptacle.

In certain embodiments, a method of producing a flexible circuit for insertion into a pill capsule can include producing a first portion having a first electrical contract to electrically connect with a first terminal of a battery and producing a second portion, positioned parallel to the first portion, having a second electrical contact to electrically connect with a second terminal of the battery. The method can also include producing a first arm, having a length separating the first portion and the second portion, positioned between the first portion and the second portion and positioned perpendicular to the first portion and to the second portion.

The method can also include producing a third portion to be positioned on a first side of a cube ferrite core. Furthermore, the method can include producing a fourth portion positioned on a second side of the cube ferrite core and positioned perpendicular to the third portion. The method can also include producing a fifth portion positioned on a third side of the cube ferrite core and positioned perpendicular to the third portion and to the fourth portion. The third portion can include a first antenna to generate a first transmit signal in a first direction. The fourth portion can include a second antenna to generate a second transmit signal in a second direction. The fifth portion can include a third antenna to generate a third transmit signal in a third direction.

Additionally, in certain embodiments, the first direction can be substantially perpendicular to the second direction and the third direction, the second direction can be substantially perpendicular to the first direction and third direction, and the third direction can be substantially perpendicular to the first direction and the second direction. Moreover, the method can also include inserting the battery to electrically connect the first terminal of the battery with the first electrical contact and to electrically connect the second terminal of the battery the second electrical contact. Furthermore, the method can also include inserting the cube ferrite core with the third portion positioned on the first side of the cube ferrite core, the fourth portion positioned on the second side of the cube ferrite core, and the fifth portion positioned on the third side of the cube ferrite core.

BRIEF DESCRIPTION OF THE DRAWINGS

Throughout the drawings, reference numbers are used to indicate correspondence between referenced elements. The drawings are provided to illustrate embodiments of the features described herein and not to limit the scope thereof.

FIG. 1 illustrates an embodiment of a capsule including components that generate, transmit, receive, and process a dipole magnetic field.

FIGS. 4A-4C illustrate another embodiment of a pill circuitry.

FIGS. 5A-5B illustrate another embodiment of a pill circuitry

FIGS. 12A-12B illustrate the body antenna circuitry of FIGS. 11A-11B.

DETAILED DESCRIPTION

Figures 2A, 2B:
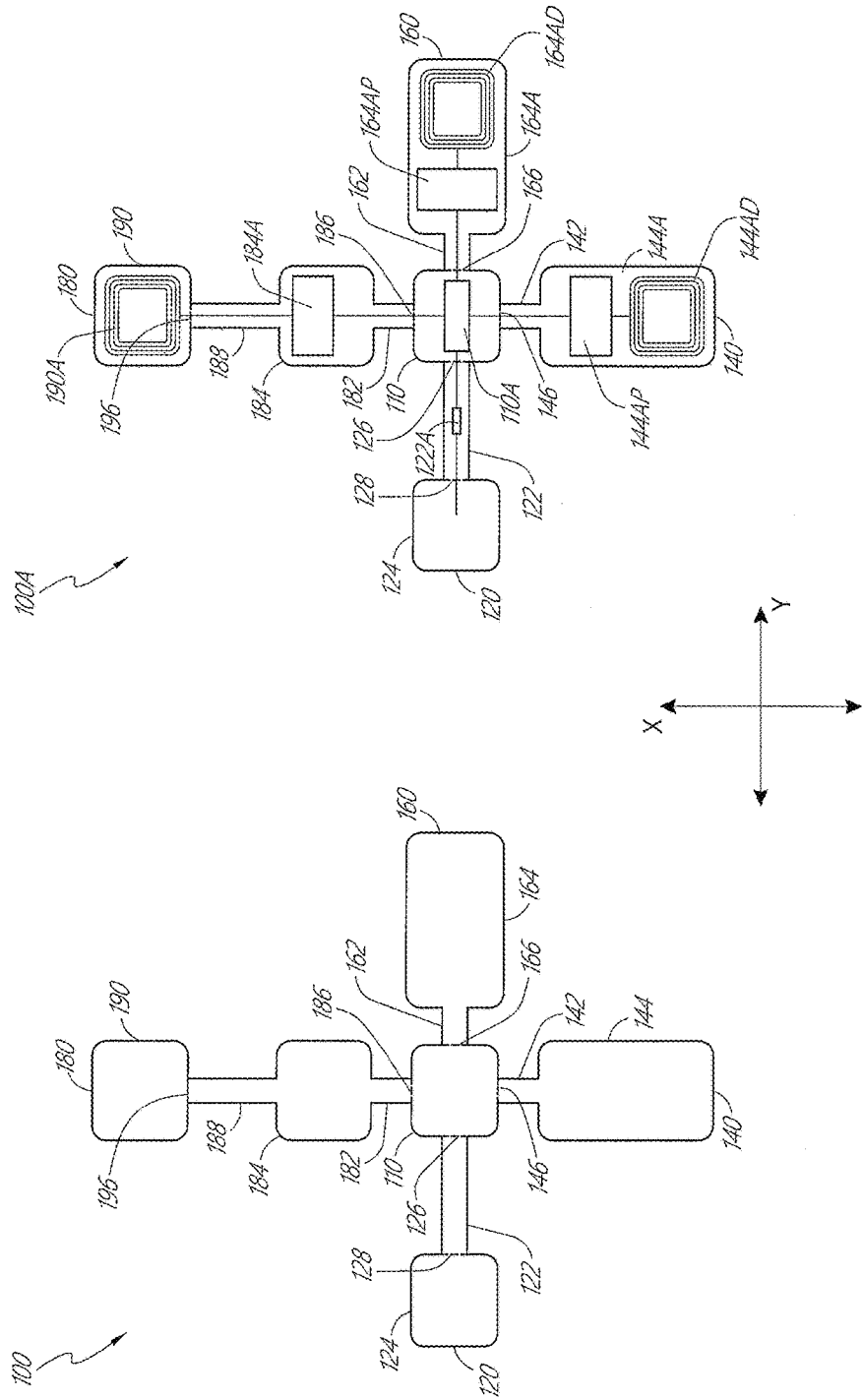
FIGS. 2A-2C illustrate an embodiment of a pill circuitry.

The gastrointestinal (GI) tract has become an increasingly important area of study as more related discoveries to public health and disease are made. However, as progress is made, our knowledge is limited by our technology as we are unable to adequately study and understand individual patient's GI systems. As such, there is a need for technological growth in the area of GI tract research that is highly efficient, cost efficient, noninvasive, and easily implemented for proper diagnosis and further research in GI motility. Embodiments of the systems described herein can provide such advantages to advance diagnosis, treatment, research, and monitoring of a wide range of GI diseases and conditions.

The embodiments in this disclosure relate to integration of electronics in an ingestible unit, such as a capsule. Once swallowed, the capsule can travel through the GI tract including the mouth, esophagus, stomach, small intestine, large intestine, colon, rectum, and anus, until it is ultimately eliminated from the human body. The electronics inside the capsule can include at least one antenna that can transmit a signal as it travels through the GI tract, which can be detected by at least one magnetic field sensor (body antennas). The body antennas are described more in detail in U.S. Pub. No. 2015/0112189, entitled "NEARLY ISOTROPIC DIPOLE ANTENNA SYSTEM," filed on Oct. 21, 2014, the entire content of which is incorporated herein for all purposes by reference. Signals collected by the body antennas are sent to a modular electronics unit (MEU) for determination of the location of the capsule. In addition, the signal acquisition and determination is described more in detail in (and is incorporated by reference in its entirety and for all purposes of the subject matter disclosed in each of the following applications): U.S. Pub. No. 2015/0112189, entitled "NEARLY ISOTROPIC DIPOLE ANTENNA SYSTEM," filed on Oct. 21, 2014, and U.S. Pub. No. 2015/0196229, entitled "SYSTEM AND METHODS FOR TRIGGERING A RADIOFREQUENCY TRANSCEIVER IN THE HUMAN BODY," filed on Mar. 24, 2015.

While the current systems and methods are discussed with respect to a pill or capsule that can be ingested by a human or animal, the systems and methods can also be used in other application for determination of location. The location of the pill can be determined by magnetic field sensors worn on or placed near the patient's body. In an embodiment, the pill motion can be tracked to determine if there are any gastrointestinal motility abnormalities, directional flow issues, intestinal blockages, or any other related conditions. In addition to real time location, the pill's flow rate, orientation, rotation, and other measurements can also be tracked and monitored, relevant to the diagnosis of conditions and study of the GI tract.

Thus, the systems and methods described herein can provide clinicians with the ability to identify obstructions, regurgitations, reflux, peristalsis, or other GI conditions that are dangerous to a patient's health and which are currently difficult if not impossible to monitor in a simple, low cost, real time, and non-invasive manner. Thus, the systems and methods described herein can facilitate diagnosing and/or treating numerous diseases and conditions, including, but not limited to, Crohn's disease, diverticulitis, angiodysplasias, colorectal cancer, inflammatory bowel diseases, bowel strangulation, neuropathy, paraplegia-related conditions, diabetic gastroparesis, functional dyspepsia, irritable bowel syndrome, epigastric pain syndrome, and post infectious and idiopathic gastroparesis. Further, the systems and methods described herein can facilitate treating patients with endocrine disorders such as hypo-/hyperthyroidism, pituitary and parathyroid disease, and Addison's disease.

Embodiments of the pill can be used in the systems and methods described in the incorporated references, which include transmitting elements for transmitting signals towards the receiving body antennas.

There is a need for a capsule capable of being tracked that is small enough to be swallowed without causing significant discomfort to the patient while being swallowed and while traveling through the patient's GI tract. There is also a need for a capsule capable of being tracked that can maintain a battery life through the digestive cycle, including abnormal digestive cycles where the cycle occurs at a slower rate. There is also a need for a capsule capable of being tracked to be compact enough to simulate the motion and flow of the food particles as they would naturally break down through the body. The digestive system naturally breaks down food particles and as such, there is a need for the capsule to be compact and appropriately sized to mimic food and waste to properly study GI abnormalities and diseases.

Similarly, there is also a need for a pill capsule capable of being tracked to be minimally weighted for the capsule to travel through the body easily, replicating the movement of liquid, food, and waste through the GI tract. Similarly, there is also a need for a pill capsule of appropriate buoyancy for the pill capsule to move with the gases or fluid in the lumen of the GI tract. For example, the pill can be manufactured with a neutral buoyancy such that the pill has the same density as the fluid it is immersed in. The pill can be manufactured with a negative buoyancy such that the pill is denser than the fluid it is immersed in and will therefore sink in the fluid. The pill with a negative buoyancy with travel with the liquids in the lumen of the GI tract. The pill can also be manufactured with a positive buoyancy such that the pill is less dense than the fluid it is immersed in. The pill with a positive buoyancy can travel with the gasses in the lumen of the GI tract. The pill can be manufactured with a particular buoyancy to move with the gasses or fluid of the GI tract depending on the type of GI condition of interest.

In addition to the location tracking, there is a need for a capsule in which the orientation, rate of movement, rotation, direction of travel, and other measurements can be determined and monitored. These measurements can help study the mechanisms of the GI tract such as the stretching and contracting of the GI tract as well as other movements of the GI tract.

FIG. 1 illustrates an embodiment of a capsule 10 that is designed to be tracked as it travels through a patient's GI tract once swallowed. The capsule 10 can include structural components for determining and monitoring measurements. For example, the capsule 10 can include a ferrite core 30. The ferrite core may be optional in some embodiments. The capsule 10 can further include at least one antenna. In some embodiments, the capsule 10 includes three antennas. In further embodiments, the capsule 10 includes more than three antennas or less than three antennas. An example of ferrite core and antenna arrangement is described more in detail below.

The flexible circuit 100 can include a flexible circuit structure that can be formed in a particular arrangement. The flexible circuit structure can be arranged and folded to a compact size suitable for pill encapsulation and ingesting by a patient. The flexible circuit structure can also be arranged to reduce the electrical interference with the battery and electronics as described more in detail below.

The flexible circuit 100 can house several circuit elements. The circuit elements can include pulse forming and generation circuits. The circuit elements can further include amplification, filtering and power conditioning circuit elements. The electronic circuits can generate pulses of magnetic or electromagnetic fields to be orthogonally directed and transmitted by the one or more antennas and detected by external magnetic field sensors or body antennas as discussed below.

These circuits are arranged in a particular design on a flexible circuit board that allows fitting and packaging into a small capsule 10 that a patient can swallow or ingest. Capsule electronics can include a programmable hardware processor that can generate a pulse of a certain amplitude, frequency, pulse duration, pulse repetition pattern, and pulse spacing. In some embodiments, the programmable hardware processor can generate pulses for up to 3 substantially orthogonal antenna directions. An amplifier circuit can increase each pulse signal strength. The ferrite core 30 can also amplify the signal. The battery 20 can provide power to the capsule electronics. The capsule electronics can include power conditioning and filtering circuitry.

Pill Design

Figure 2C:
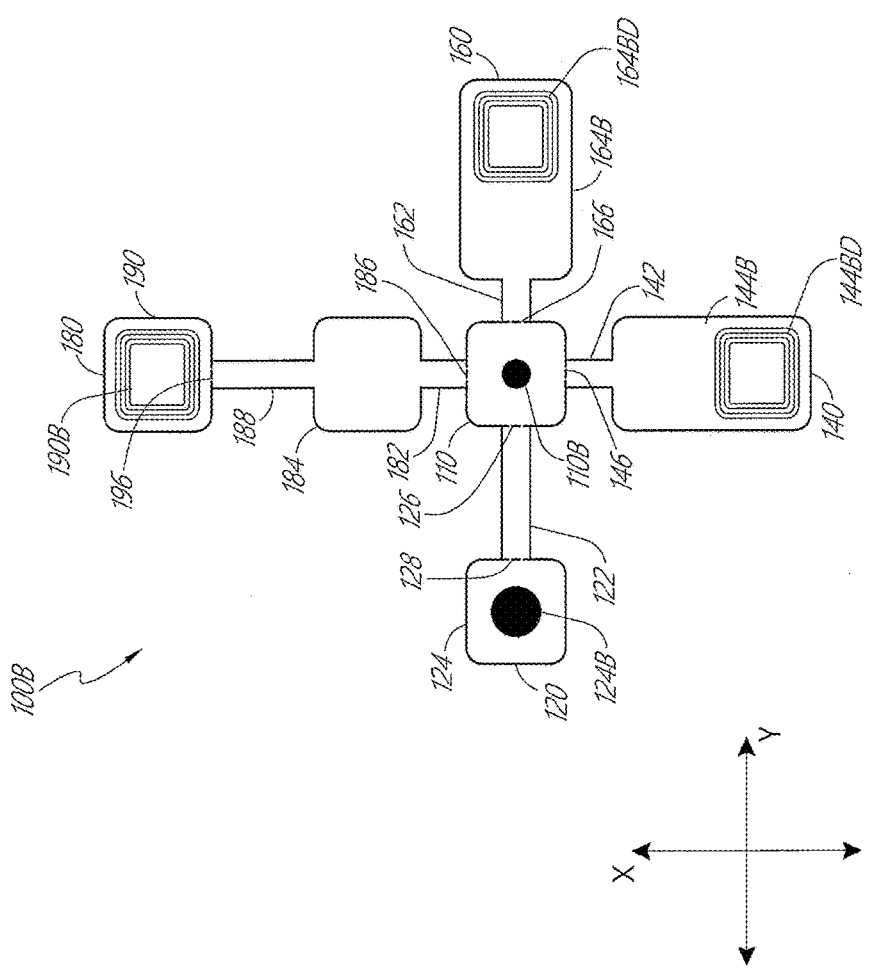

FIGS. 2A-2C illustrate an embodiment of a flexible circuit 100 in an unfolded configuration. FIG. 2A illustrates the flexible circuit 100 in an unfolded configuration. FIG. 2B illustrates the capsule electronics of the top side 100A of the pill circuitry in an unfolded configuration. FIG. 2C illustrates the capsule electronics of the bottom side 100B of the pill circuitry in an unfolded configuration.

In some embodiments, the flexible circuit 100 can include circuitry on both sides of the flexible circuit 100 to maximize the surface area for mounting circuits and to minimize the size of the folded flexible circuit. The type of circuits placed on a particular side can be selected based on space and interference constraints. In other embodiments, the flexible circuit 100 can include circuitry mounted only one side for ease of printing, folding, mass production, and lower production costs. In some embodiments, the flexible circuit 100 can included circuitry mounted on both sides to reduce the size of the folded flexible circuit 100. In some embodiments, the antennas 144BD, 164BD, 190B are positioned on the flexible circuit 100 to reduce interference with the battery 20 and electronics as discussed more in detail in the incorporated references.

Figure 3C:
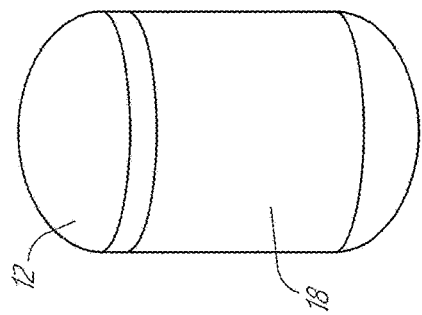
FIG. 3C illustrates the pill capsule including pill circuitry, ferrite core, and battery.
Figure 3B:
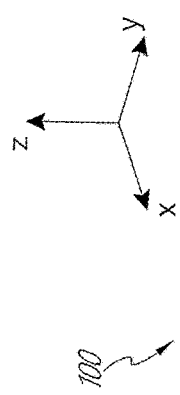
FIG. 3B illustrates the pill circuitry of FIG. 2 in an intermediate folded configuration to incorporate a ferrite core and battery.

In some embodiments, the folded flexible circuit 100 can be arranged such that the electronics can be positioned on the outside surface of the folded flexible circuit as shown in FIG. 3B. This can provide ease of repair and testing of the pill electronics without having to unfold the flexible circuit 100. The signal generation circuits drive the NIDA cube coils, which can be affixed by epoxy or by other appropriate adhesive to the three sides of the ferrite cube 30. The flexible circuit 100 can be folded such that the top side 100A can be facing outward such that the outside surface of the folded flexible circuit 100 is the top side 100A and the inside surface of the folded flexible circuit 100 is the bottom side 100B.

As shown in FIG. 2B, the capsule electronics can include one or more Hartley or similar pulse generating oscillators 184A, 164AP, 144AP, an embedded programmable microcontroller 110A, a photodiode switch 122A to start and stop the circuitry, one or more batteries 20, and a ferrite core 30 on a flexible circuit 100. The flexible circuit 100 can include three Hartley oscillators or similar pulse generating oscillators 144AP, 164AP, 184A. The Hartley oscillators can be positioned on three different branches 140, 160, 180 to minimize interference between the oscillators 144AP, 164AP, 184A. The microcontroller 110A can be positioned on the top side 100A of the central body portion 110. When the flexible circuit 100 is folded as shown in FIG. 3B, the microcontroller 110A can be positioned on the outside surface of the folded flexible circuit 100. This can provide ease of manufacturing and repair of the microcontroller 110A without having to unfold the flexible circuit 100. The flexible circuit 100 can include a photodiode switch 122A on the top side 100A of the arm 122. When the flexible circuit 100 is folded as shown in FIG. 3B, the photodiode 122A can be on the outside surface such that it is easily accessible for light to be applied to activate the pill electronics during the initial pill activation process 600 as discussed more below. The folded flexible circuit 100 can be inserted into a pill capsule 10 that is transparent or semi-transparent such that a light source can be applied to the photodiode 122A.

Figure 3A:
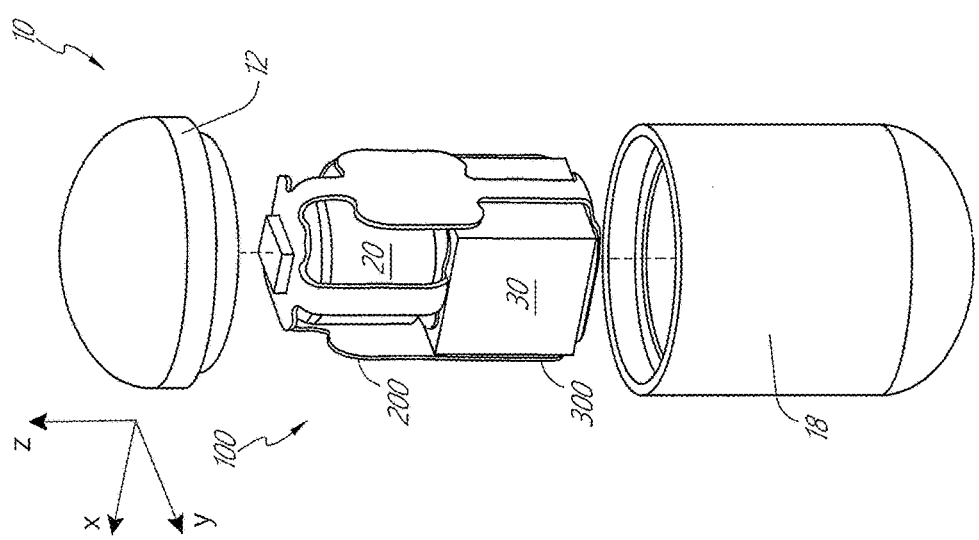
FIG. 3A illustrates the pill circuitry of FIG. 2 in a folded configuration for insertion into the capsule.

As shown in FIG. 2C, the flexible circuit 100 includes three antenna portions 144BD, 164BD, 190B. The antenna portions 144BD, 164BD, 190B can include loop antenna as disclosed in the incorporated patent references. The loop antennas like all other electronics can be printed. The flexible circuit 100 includes a positive terminal portion 110B and a negative terminal location 124B. In an embodiment, the flexible circuit 100 wraps around the battery 20 such that both the terminals 110B, 124B are connected to the positive and negative terminals of the battery 20 as shown in FIGS. 3A-B.

As shown in FIG. 2A, the flexible circuit 100 can include four branches 120, 140, 160, 180 that extend from a central body 110. Proximal can be defined as towards the central body 110 and distal can be defined as away from the central body 110. The first branch 120 can include an electronics region 124 that can be positioned at the distal end. The first branch 120 may include an arm 122 positioned between the central body 110 and the electronics region 124. The arm 122 can be positioned proximal to the electronics region 124 and distal to the central body 110. The central body 110 can include a positive terminal portion 110B on the bottom side 100B of the flexible circuit 100. The electronics region 124 can include a negative terminal portion 124B on the bottom side 100B on the flexible circuit 100.

The second branch 140 can include an electronics region 144 positioned at the distal end. The second branch 140 can also include an arm 142 positioned between the electronics region 144 and the central body 110. The arm 142 can be positioned proximal to the electronics region 144 and distal to the central body 110. As shown in FIG. 2B, the top side 100A of the electronics region 144A can include a proximal portion 144AP and a distal portion 144AD. The Hartley oscillator 144AP can be positioned on the top side 100A of the proximal portion 144AD of the electronics region 144. As shown in FIG. 2C, the bottom side 100B of the electronics region 144 can include a proximal portion 144BP and a distal portion 144BD. The antenna portion 144BD can be positioned on the bottom side 100B of the distal end 144BD of the electronics region 144.

The third branch 160 can include an electronics portion 164 at the distal end. The third branch 160 can include an arm 162 positioned between the central body 110 and the electronics portion 164. The arm 162 can be positioned proximal to the electronics portion 164 and distal to the central body 110. As shown in FIG. 2B, the top side 100A of the electronics region 164A can include a proximal portion 164AP and a distal portion 164AD. The Hartley oscillator 164AP can be positioned on the top side 100A of the proximal portion 164AP of the electronics region 144. As shown in FIG. 2C, the bottom side 100B of the electronics region 164 can include a proximal portion 164BP and a distal portion 164BD. The antenna portion 164BD can be positioned on the bottom side 100B of the distal end 164BD of the electronics region 164.

The fourth branch 180 can include two electronics regions: a proximal electronics region 184 and the distal electronics region 190. The fourth branch 180 can include a proximal arm 182 between the central body 110 and the proximal electronics region 184. The proximal arm 182 can be positioned proximal to the proximal electronics region 184 and distal to the central body 110. The fourth branch 180 can include a distal arm 188 positioned between the proximal electronics region 184 and the distal electronics region 190. The distal arm 188 can be positioned proximal to the distal electronics portion 190 and distal to the proximal electronics region 184. The proximal electronics region 184 can include power electronics and driving circuitry 184B on the bottom side 100B of the flexible circuit 100. The distal electronics region 190 can include an antenna portion 190B on the bottom side 100B of the flexible circuit 100.

In the unfolded configuration as shown in FIGS. 2A-B, the center body 110 and the four branches 120, 140, 160, 180 can lie in an x-y plane or two-dimensional plane with the center body 110 as the center. The x-axis can be defined along the longitudinal axis of the unfolded flexible circuit 100 as shown in FIGS. 2A-B. The second branch 140 and fourth branches 180 can lie substantially parallel to the longitudinal axis of the unfolded flexible circuit 100 or the along the x-axis in either direction from the center body 110. The y-axis can be defined perpendicular to the x-axis and perpendicular to the longitudinal axis of the unfolded flexible circuit 100. The first branch 120 and third branch 160 can lie substantially perpendicular to the longitudinal axis of the unfolded flexible circuit 100 or substantially parallel to the y-axis in either direction from the center body 110. The z-axis can be defined as an axis orthogonal to both the x-axis and the y-axis.

The flexible circuit 100 is folded and inserted into the pill outer capsule units 18, 12, as shown in FIGS. 3A-3C. The folding process 600 is described more below in FIG. 6. The z-axis can be defined along the longitudinal axis of the pill capsule 10 as shown in FIG. 3A. The z-axis can also be defined along the longitudinal axis of the folded flexible circuit 100 as shown in FIGS. 3A-B. This z-axis of the folded flexible circuit 100 is then aligned with the z-axis of the pill capsule 10 when inserted.

Each of the four branches 120, 140, 160, 180 can be folded at the first arm such that the length of each arms extend in a direction substantially parallel to the z-axis. The first branch 120 can be folded such that the length of the arm 122 and the length of the electronics region 124 extend parallel to the z-axis. The width of the electronics region 124, which is perpendicular to the length of the electronics region 124, can extend parallel to the x-axis.

The first branch 120 can be folded again such that the electronics region 124 may lie in a plane parallel to the x-y plane. The electronics region 124 has a bottom side 124B on the bottom side 100B of the flexible circuit 100. The central body 110 also has a bottom side 100B of the flexible circuit 100. The electronics region bottom side 124B can be positioned to face the central body bottom side 110б.

The surfaces of the folded flexible circuit 100 can be defined by a normal line which is perpendicular to the surface of the folded flexible circuit 100. The normal line of the bottom side 100B of the electronics region 124B can be substantially parallel to the positive z-axis. The normal line of the bottom side 100B of the arm 122B can be substantially parallel to the positive y-axis. The normal line of the bottom side 100б of the central body 110б can be substantially parallel to the negative z-axis. [0047] The second branch 140 can be folded such that the electronics region 144 extends substantially parallel to the z-axis. The width of the electronics region 144, which is perpendicular to the length of the electronics region 144, can extend parallel to the y-axis. The normal line of the electronics region 144 can be substantially parallel to the x-axis.

The third branch 160 can be folded such that the length of the electronics region 164 extends substantially parallel to the z-axis. The width of the electronics region 164, which is perpendicular to the length of the electronics region 164, can extend parallel to the x-axis. The normal line of the electronics region 164 can be substantially parallel to the y-axis.

The bottom surface 100B of the first branch arm 122B and the bottom surface 100B of the third branch electronics region 164B may be positioned to face each other. The normal line of the bottom side 100B of the first branch arm 122B may be substantially parallel to the positive y-axis. The normal line of the bottom side 100B of the third branch electronics region 164B may be substantially parallel to the negative y-axis.

The bottom surface 100B of the second branch electronics region 144B and the bottom surface 100B of the fourth branch proximal electronics region 184б may be positioned to face each other. The bottom surface 100б of the second branch electronics region 144B and the bottom surface 100B of the fourth branch distal arm 188B may be positioned to face each other. The second branch electronics region 144, the fourth branch proximal electronics region 184, and the fourth branch distal arm 188 can each lie in a plane parallel to the y-z plane. The normal line of the bottom side 100B of the second branch electronics region 144B can be substantially parallel to the positive x-axis. The normal line of the bottom side 100B of the fourth branch proximal electronics region 184B can be substantially parallel to the negative x-axis. The normal line of the bottom side 100б of the fourth branch distal arm 188B can be substantially parallel to the negative x-axis.

The fourth branch 180 can be folded such that the length of the proximal electronics region 184, the distal arm 188 and the distal electronics region 190 extend substantially parallel to the z-axis. The width of the proximal electronics region 184, the distal arm 188 and the distal electronics region 90, perpendicular to their respective lengths, can extend parallel to the y-axis.

The fourth branch 190 can be folded again such that the distal electronics region 190 may lie in a plane parallel to the x-y plane. The electronics region 190 has a bottom side 190B on the bottom side 100B of the flexible circuit 100. The electronics region 124 has a top side 124A on the top side 100A of the flexible circuit 100. The bottom side 100B of the electronics region 190B can be positioned to face the electronics region 124A. The normal line of the bottom side 100B of the fourth branch distal electronics region 190B can be substantially parallel to the negative z-axis. The normal line of the top side 100A of the first branch electronics region 124A can be substantially parallel to the negative z-axis.

The central body 110, the first branch electronics region 124, the fourth branch distal electronics region 190 can each lie in planes parallel to the x-y plane. The central body 110 and the first branch electronics region 124 may lie in planes parallel to each other and properly spaced from each other to receive the battery 20. The folded circuit 100 can be arranged such that the bottom side 100B of the central body 110б and the bottom side 100б of the first branch electronics region 124B face each other. The folded circuit 100 can be arranged such that the bottom side 100B of the central body 110б and the bottom side 100B of the first branch electronics region 124B face the battery 20 once inserted. The normal line of the bottom side 100B of the central body 110B can be substantially parallel to the negative z-axis. The normal line of the top side 100A of the central body 110A can be substantially parallel to the positive z-axis. The normal line of the bottom side 100B of the first branch electronics region 124B can be substantially parallel to the positive z-axis. The normal line of the bottom side 100B of the first branch electronics region 124B can be substantially parallel to the positive z-axis.

The first branch electronics region 124 and the fourth branch distal electronics region 190 may lie in planes parallel to each other and properly spaced from each other to receive the ferrite core 30. The first branch electronics region 124 and the fourth branch distal electronics region 190 may lie in planes parallel to each other and properly spaced from each other to receive the ferrite core 30. The folded circuit 100 can be arranged such that the bottom side 100B of the central body 110B and the bottom side of the first branch electronics region 124B face each other. The folded circuit 100 can be arranged such that the top side 100A of the first branch electronics region 124A and the bottom side 100B of the fourth branch distal electronics region 190B face the ferrite core 30 once inserted. The normal line of the bottom side 100B of the central body 110B can be substantially parallel to the negative z-axis. The normal line of the bottom side 100B of the first branch electronics region 124B can be substantially parallel to the positive z-axis. The normal line of the bottom side 100B of the electronics region 190B may be substantially parallel to the positive z-axis.

FIGS. 3A-3C illustrate the pill circuitry in a folded configuration for insertion into a capsule. The flexible circuit 100 shown in FIGS. 3A-3B can be folded to encapsulate and connect to the battery 20 and ferrite core 30 such that the components can be inserted into a pill capsule 10. The flexible circuit 100 can be folded in a configuration such that the three antennas 144BD, 164BD, 190B, can transmit in nearly orthogonal directions as discussed in the above incorporated patent references.

As shown in FIGS. 3A-3B, the folded flexible circuit 100 can be arranged such that there are two levels: a top level 200 and a bottom level 300 of the folded flexible circuit 100 along the z-axis. Each level 200, 300 of the folded flexible circuit 100 can include a cavity for components. In some embodiments, the folded flexible circuit 100 can include a single cavity for components. In some embodiments, the folded flexible circuit 100 can include two or more cavities for components.

The battery or set of batteries 20 reside in the cavity of the top level 200 of the folded flexible circuit 100. The folded flexible circuit 100 can be arranged such that the positive terminal portion 110B and negative terminal portion 124B of the flexible circuit 100 are positioned in the cavity of the top level 200. The positive terminal portion 110B and the negative terminal portion 124B may be positioned for electrical connection with the terminal ends of the battery 20.

The battery 20 can be a single battery or a combination of multiple batteries. In some embodiments, the battery 20 can be a 1.55 V battery, a 1.5 V battery, a 3.0 V battery, or a 3.6 V battery. In some embodiments, the battery 20 can be coin shaped with a diameter of approximately 4 mm to approximately 6 mm. In some embodiments, the battery 20 can be coin shaped with a height of approximately 1 mm to approximately 3 mm. In some embodiments, the folded up flexible circuit 100 can be approximately square or rectangular with dimensions from approximately 5 mm to approximately 20 mm. In some embodiments, the life of the battery can last for up to 5 days. In other embodiments, the life of the battery can last for up to 10 days. For other embodiments, the life of the battery can last longer than 10 days. The extended life of the battery 20 can enable the pill 10 to be tracked and monitored through the entire digestive cycle.

The ferrite core 30 can be inserted in the cavity of the bottom level 300 of the folded flexible circuit 100. The antenna portions 144BD, 164BD, 190B can be positioned in the bottom level 300 of the folded flexible circuit 100. The antenna portions 144BD, 164BD, 190B can be positioned to surround the ferrite core 30. The antenna portions 144BD, 164BD, 190B can be positioned to transmit in three substantially orthogonal directions of the ferrite core 30. The normal lines of the antenna portions 144BD, 164BD, 190B can be substantially orthogonal to each other. The normal line of the antenna portion 144BD can be substantially parallel to the x-axis. The normal line of the antenna portion 164BD can be substantially parallel to the y-axis. The normal line of the antenna portion 190B can be substantially parallel to the z-axis.

In other embodiments, an antenna portion may be positioned on the top side 100A of the first branch electronics region 124A. In the folded configuration, the antenna portion 124A may lie in a plane substantially parallel to the x-y plane. In the folded configuration, the antenna portion 124A may lie between the battery 20 and the ferrite core 30. The flexible circuit 100 may include two other antenna portions to transmit in three substantially orthogonal directions of the ferrite core 30.

In some embodiments, the folded flexible circuit 100 may be a single unit or single body with two or more levels. The folded flexible circuit 100 may have one or more cavities for components. The flexible circuit can be partitioned, if necessary, by functional unit. In other embodiments, the folded flexible circuit 100 may include several subparts, units, or bodies that are connected. This makes each section capable of being tested, repaired, replaced, or manufactured separately. Further, the distinct subparts may provide ease of folding and flexibility of arrangement. The separation of subparts can also provide ease of testing or replacement such that the pill electronics can be tested and repaired without disturbing other components of the pill electronics. The various subparts can also be activated separately for efficiency and battery conservation. For example, the folded flexible circuit 100 can include separate subparts wherein there are multiple camera assemblies, a tracking assembly, actuators and other sensors. In some embodiments, the flexible circuit 100 can include two or more branches. In other embodiments, the flexible circuit 100 can include more than four branches or other configurations to include various electronic components and assemblies.

In some embodiments, the folded flexible circuit 100 can be configured to only surround the ferrite core 30. The battery 20 can be positioned outside the cavity of the folded flexible circuit 100 and connected to the folded flexible circuit 100.

The pill capsule electronics and circuit traces, which allow electricity to flow between electronic components, can be positioned and designed on the flexible circuit 100 to ensure isolation among traces such that traces do not touch or short. Similarly, the circuit traces on the flexible circuit 100 can be positioned and designed such that they do not break at the folds of the flexible circuit. The size of the flexible circuit 100 and the size of the outer pill capsule 10 can be optimized such that there is adequate compression of the flexible circuit 100. Adequate compression can ensure the battery 20 and other components make sufficient contact with the flexible circuit 100. The optimization of the size of the outer pill capsule and the flexible circuit 100 can also minimize the size of the capsule for ease of swallowing. Similarly, the antenna portions 144BD, 164BD, 190B, can be optimally sized to maximize signal emission to body antennas.

The flexible circuit 100 is shown in the folded configuration in FIGS. 3A-B. In an embodiment, the flexible circuit 100 can be arranged and laid out in a pattern to allow the circuits to fold up into a compact configuration as shown in FIG. 1 and FIGS. 3A-B. In some embodiments, the folded flexible circuit 100 can be approximately square with dimensions from approximately 5 mm to approximately 20 mm. In some embodiments, the folded flexible circuit 100 can be rectangular with each side having dimensions of approximately 5 mm to approximately 20 mm. In some embodiments, the folded flexible circuit 100 can be no larger than approximately 15 mm in any dimension. In some embodiments, the folded flexible circuit 100 can be approximately 15 mm by approximately 6 mm by approximately 6 mm.

The central body 110 can be approximately square with dimensions of approximately 5.5 mm. In other embodiments, the central body 110 can be approximately square with dimensions of approximately 5 mm to 6 mm. In some embodiments, the central body 100 can be approximately square with dimensions of approximately 4 mm to 10 mm. In other embodiments, the central body 110 can be also be round, triangular, or another shape.

The electronics regions 144, 164, can each have a length of approximately 10.5 mm and a width of approximately 6 mm. In some embodiments, the lengths of the electronics regions 144, 164, can range from approximately 5 mm to approximately 20 mm. In other embodiments, the electronics regions 144, 164 can be also be round, triangular, or another shape.

The arms 142, 162, 182 can each have a length of approximately 2.5 mm. In some embodiments, the lengths of the arms 142, 162, 182, can range from approximately 1 mm to approximately 10 mm. The first branch arm 122 can have a length of approximately 6.5 mm. In some embodiments, the length of the first branch arm 122 can range from approximately 1 mm to approximately 10 mm. The fourth branch distal arm 188 can have a length of approximately 5 mm. In some embodiments, the length of the fourth branch distal arm 188 can range from approximately 1 mm to approximately 10 mm.

In some embodiments, the arms 122, 142, 162, 182, 188 can have a substantially smaller width than the central body 110 and the electronics regions 144, 164, 184, 190. The smaller width of the arms 122, 142, 162, 182, 188 can facilitate easy folding of the flexible circuit 100. In other embodiments, the arms 122, 142, 162, 182, 188 can have substantially the same width as the central body 110 and the electronics regions 144, 164, 184, 190.

The fourth arm proximal electronics region 184 can be approximately square with dimensions of approximately 6 mm. In some embodiments, the fourth arm proximal electronics region 184 can be approximately square with dimensions of approximately 4 mm to 10 mm. In other embodiments, the fourth arm proximal electronics region 184 can be also be round, triangular, or another shape.

The fourth arm distal electronics region 190 can be approximately square with dimensions of approximately 6 mm. In some embodiments, the fourth arm distal electronics region 190 can be approximately square with dimensions of approximately 4 mm to 10 mm. In other embodiments, the fourth arm distal electronics region 190 can be also be round, triangular, or another shape.

The first branch electronics region 124 can be approximately square with dimensions of approximately 6 mm. The first branch electronics region 124 can be approximately square with dimensions of approximately 4 mm to 10 mm. In other embodiments, the first branch electronics region 124 can be also be round, triangular, or another shape.

The folded flexible circuit 100 can have a height of approximately 13 mm. The folded flexible circuit can have a substantially square base with dimensions of approximately 6 mm. As discussed above, the folded flexible circuit 100 can be configured such that there is an internal cavity for the ferrite core 30 and the battery 20. In other embodiments, the folded flexible circuit 100 can be configured such that there are several internal cavities for the ferrite core 30 and the battery 20. The folded flexible circuit 100, the size of the battery 20, and the size of ferrite core 30 can be optimized such that the amount of free space is minimized. The volume of the folded flexible circuit 100 can therefore be approximately 468 mm$^3$. The ferrite core 30 can be approximately cube with dimensions of approximately 6 mm. Therefore the volume of the ferrite core can be approximately 216 mm$^3$. The battery 20 can be a set of two coin batteries. The batteries 20 can have a height of approximately 5.5 mm and a diameter of approximately 6.0 mm. Therefore the volume of the battery 20 can be approximately 155.5 mm$^3$. In one embodiment, the difference between the volume of the folded flexible circuit 100 and the combined volume of the ferrite core 30 and the battery 20 is less than or equal to approximately 20%. In other embodiments, the volume of the folded flexible circuit 100 and the combined volume of the ferrite core 30 and the battery 20 is less than or equal to approximately 10%.

This folded configuration can slide into a small, ingestion-sized polycarbonate capsule 10. The pill capsule 10 can have a circular cross section with a diameter of approximately 4 mm to approximately 10 mm. The pill capsule 10 can have a length of approximately 10 mm to approximately 25 mm. The pill capsule 10 can have a length of approximately 20 mm. The pill capsule 10 can have a circular cross section of a diameter of approximately 12.7 mm. Therefore, the volume of the pill capsule 10 can be approximately 2533 mm$^3$.

In other embodiments, the pill capsule 10 can have a circular cross section of diameter of approximately 6 mm to approximately 15.

The mass of the pill capsule 10 including electronics can be approximately 2 grams. In other embodiments, the mass of the pill capsule 10 including electronics can be approximately less than 1 gram. In other embodiments, the mass of the pill capsule 10 can be approximately 1 gram to approximately 3 grams.

The density of the pill capsule 10 can be approximately 0.789 g/cm$^3$. In other embodiments, the density of the pill capsule 10 can be approximately 1 g/cm$^3$. In other embodiments, the density of the pill capsule 10 can range from approximately 0.5 g/cm$^3$ to approximately 3 g/cm$^3$.

Figure 4C:
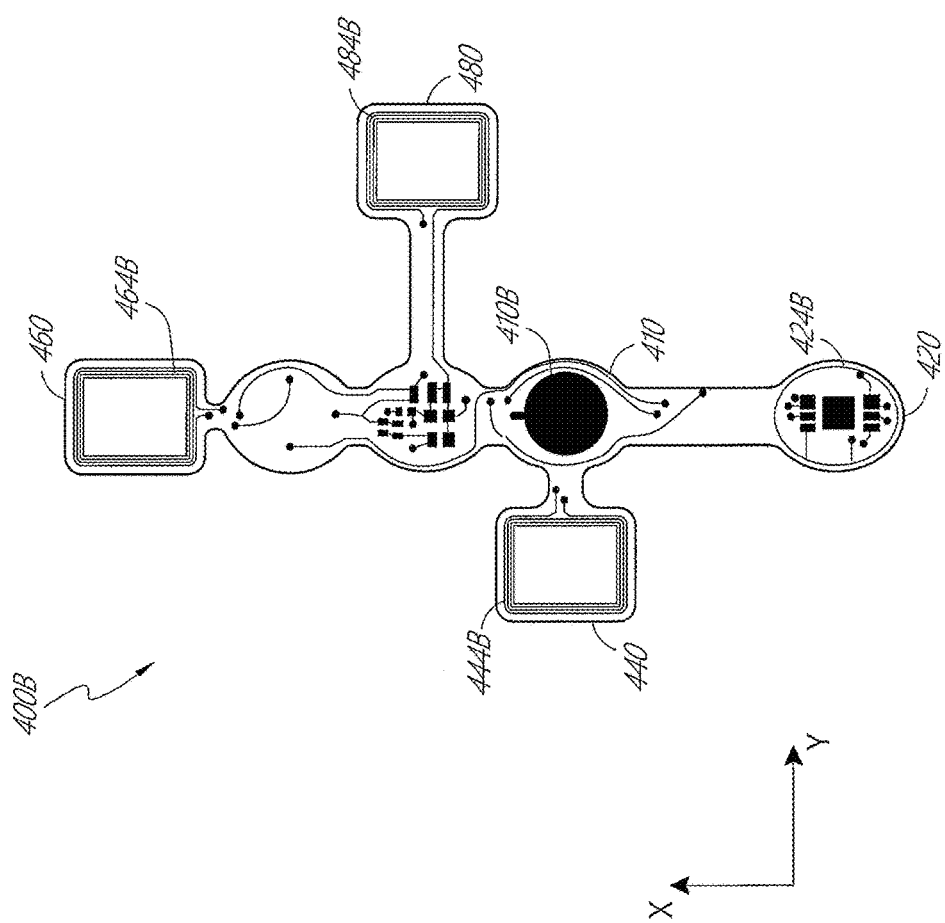

FIGS. 4A-4C illustrate another embodiment of a flexible circuit 400 in an unfolded configuration. FIG. 4A illustrates the flexible circuit 400 in an unfolded configuration. As shown in FIG. 4A, the flexible circuit 400 can include four branches 420, 440, 460, 480 that extend from a central body 410, similar to the flexible circuit 100 of FIGS. 2A-C. FIG. 4B illustrates the capsule electronics of the top side 400A of the pill circuitry of FIG. 4A. FIG. 4C illustrates the capsule electronics of the bottom side 400B of the flexible circuit 400 in an unfolded configuration. The capsule electronics can include one or more Hartley or similar pulse generating oscillators, an embedded programmable microcontroller, and a photodiode switch to start and stop the circuitry on the flexible circuit 400. The Hartley oscillators can be positioned on different branches to minimize interference between the oscillators.

As shown in FIG. 4C, the central body 410 can include a positive terminal portion 410B on the bottom side 400B of the flexible circuit 400. The electronics region 424 can include a negative terminal portion 424B on the bottom side 400B on the flexible circuit 400. The flexible circuit 400 includes a positive terminal portion 410B and a negative terminal location 424B. In an embodiment, the flexible circuit 400 wraps around a battery such that both the terminals 410B, 424B are connected to the positive and negative terminals of a battery. The flexible circuit 400 can include three antenna portions 444B, 464B, 484B. The antenna portions 444B, 464B, 484B can include loop antenna as disclosed in the incorporated patent references. In some embodiments, the antenna portions 444B, 464B, 484B are positioned on the flexible circuit 400 to reduce interference with the battery and electronics of the flexible circuit 400. In an embodiment, the flexible circuit 400 can wrap around a ferrite core such that the antenna portions 444B, 464B, 484B are secured to the ferrite core using epoxy or any other appropriate adhesive. The antenna portions 444B, 464B, 484B can be positioned to surround the ferrite core. The antenna portions 444B, 464B, 484B can be positioned to transmit in three orthogonal directions of the ferrite core.

In the unfolded configuration as shown in FIGS. 4A-B, the center body 410 and the four branches 420, 440, 460, 480 can lie in an x-y plane or two-dimensional plane with the center body 410 as the center. The x-axis can be defined along the longitudinal axis of the unfolded flexible circuit 400 as shown in FIGS. 2A-B. The y-axis can be defined perpendicular to the x-axis and perpendicular to the longitudinal axis of the unfolded flexible circuit 400. The z-axis can be defined as an axis orthogonal to both the x-axis and the y-axis. The flexible circuit 400 can be folded similar to the folding process 600 for the flexible circuit 100. The flexible circuit 400 can be folded such that the longitudinal axis of the folded flexible circuit 400 can be substantially parallel to the z-axis of the pill capsule 10. The flexible circuit 400 can be folded and inserted into the pill outer capsule units, similar to the flexible circuit 100 in FIGS. 3A-C.

FIG. 5A illustrates another embodiment of a flexible circuit 500 in an unfolded configuration. FIG. 5A illustrates the flexible circuit 500 in an unfolded configuration. As shown in FIG. 5A, the flexible circuit 500 can include three branches 540, 560, 580 that extend from a central body 510, similar to the flexible circuit 100 of FIGS. 2A-C. Proximal can be defined as towards the central body 510 and distal can be defined as away from the central body 510.

The capsule electronics can include antenna portions, one or more Hartley or similar pulse generating oscillators, an embedded programmable microcontroller, and a photodiode switch to start and stop the circuitry on the flexible circuit 400. The Hartley oscillators can be positioned on different branches to minimize interference between the oscillators. The microcontroller can be positioned on the central body portion 510. When the flexible circuit 500 is folded as shown in FIG. 5B, the microcontroller can be positioned on the outside surface of the folded flexible circuit 500. This can provide ease of manufacturing and repair of the microcontroller without having to unfold the flexible circuit 100.

The first branch 540 can include an electronics region 544 that can be positioned at the distal end. The second branch 540 can include an electronics region 564 that can be positioned at the distal end. The third branch 580 can include a proximal electronics region 584 and a distal electronics region 590. The flexible circuit 500 can include three antenna portions on the distal end of the first branch electronics region 544D, the second branch electronics region 564, and the third branch distal electronics region 590. The antenna portions 544D, 564, 590 can include loop antenna as disclosed in the incorporated patent references.

The flexible circuit 500 includes a positive terminal portion on the third branch electronics region 584 and a negative terminal location located on the proximal end of the first branch electronics region 544P. In an embodiment, the flexible circuit 500 wraps around the battery 20 such that both the terminals 584, 544P are connected to the positive and negative terminals of the battery 20 as shown in FIG. 5B.

The flexible circuit 500 is shown in the folded configuration in FIG. 5B. In an embodiment, the flexible circuit 100 can be arranged and laid out in a pattern to allow the circuits to fold up into a compact configuration as shown in FIG. 5B. FIG. 5B illustrates the pill circuitry 500 in a folded configuration for insertion into a capsule. The flexible circuit 500 shown in FIGS. 5A-B can be folded to encapsulate and connect to the battery 20 and ferrite core 30. The flexible circuit 500, the battery 20, and the ferrite core 30 can be inserted into a pill capsule 10. The flexible circuit 500 can be folded in a configuration such that the three antennas 544D, 564, 590, can transmit in nearly orthogonal directions as discussed in the above incorporated patent references.

As shown in FIG. 5B, the folded flexible circuit 500 can be arranged such that there is a single cavity for both the battery 20 and ferrite core 30. The folded flexible circuit 500 can be arranged such that the positive terminal portion 584 and negative terminal portion 544P of the flexible circuit 500 are positioned for electrical connection with the terminal ends of the battery 20. The antenna portions can be positioned to surround the ferrite core 30. The antenna portions can be positioned to transmit in three orthogonal directions of the ferrite core 30.

Folding Process

Figure 6:
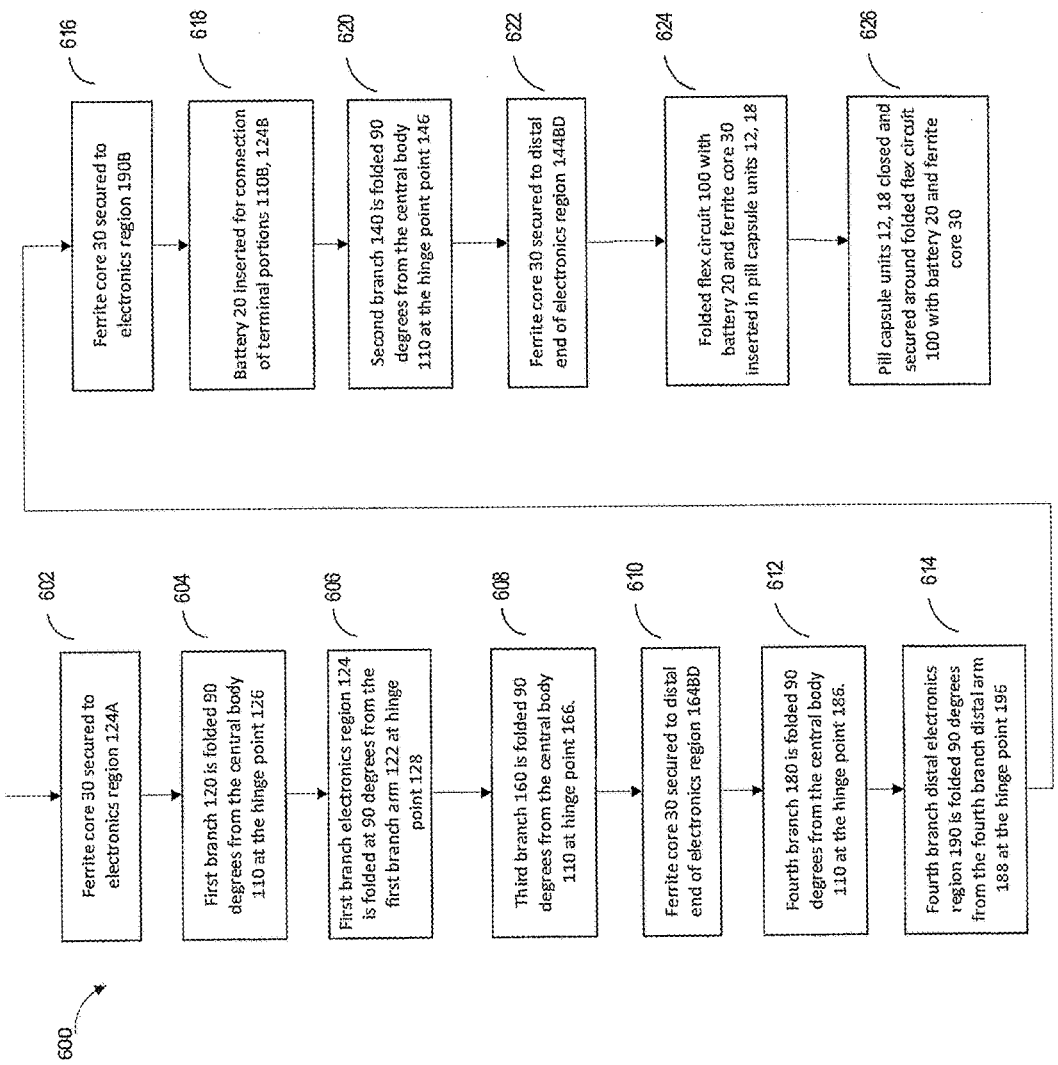
FIG. 6 illustrates an embodiment of a process for assembling the FIG. 7 illustrates a block diagram of a location tracking system for tracking a pill swallowed by a patient.

FIG. 6 illustrates an embodiment of a process 600 for folding the flexible circuit 100 and assembling the pill 10. In other embodiments, alternative arrangements of the flexible circuit 100 such as the flexible circuit 400 or the flexible circuit 500 can be folded in a compact formation to be inserted in a pill capsule 10 suitable for swallowing. The process 600 of folding can be executed by clamping the flexible circuit 100. The flexible circuit 100 can be secured to the ferrite core 30 using epoxy or other adhesive bonding. As the flexible circuit 100 is folded and positioned around the ferrite core 30, the flexible circuit 100 and the ferrite core 30 can be clamped in place for the epoxy or other adhesive bonding to cure. The epoxy can be cured for an extended period of time at room temperature or an elevated temperature or at room temperature followed by an elevated temperature. The folding process 600 can be automated or manual or a combination thereof.

As described above, the first branch arm 122 can be positioned between the center body 110 and an electronics region 124. At block 602, the ferrite core 30 can be aligned and secured on the top side 100A of the first branch electronics region 124A. The ferrite core can be secured with epoxy or any other adhesive bonding method.

At block 604, the first branch 120 can be folded at about 90 degrees at the hinge point 126 from the center body 110. The hinge point 126 can be the point where the first branch arm 122 meets the center body 110. The hinge point 126 can be positioned at the distal end of the central body 110 and at the proximal end of the first branch arm 122. As a result, the length of the first branch 120 can be substantially perpendicular the x-y plane as defined above and substantially parallel to the z-axis.

At block 606, the first branch 120 can be folded again. The first branch 120 can be folded at about 90 degrees at the second hinge point 128 from the first branch arm 122. The hinge point 128 can be the point where the first branch arm 122 meets the first branch electronics region 124. The hinge point 128 can be positioned at the proximal end of the electronics region 124 and at the distal end of the first branch arm 122. As a result, the first branch electronics region 124 can lie substantially parallel to the x-y plane. As described above, the central body 110 lies in the x-y plane. Therefore, the first branch electronics region 124 can be aligned with and lie parallel to the central body portion 110. As a result, the ferrite core 30 secured to the first branch electronics region 124B and is aligned with the center body 110. The distance between the first branch electronics region 124 and the central body portion 110 can be the length of the first branch arm 122. Similarly, the distance between the ferrite core 30 to the central body portion 110 can be the length of the first branch arm 122.

The final folded configuration of the first branch 120 can create a U shape such that the first branch 120 forms three perpendicular sides. The three sides of the U shape can be the central body 110, the first branch arm 122, and the first branch electronics region 124. The three sides of the U shape can be approximately equal in length. The two parallel sides can be the central body portion 110 and the first electronics branch region 124. The first branch electronics region 124 can lie in a plane substantially parallel to the central body 110. The bottom side 100B of the central body portion 110B can face the bottom side 100B of the first branch electronics region 124B. The two parallel sides can be approximately equal in length. The third side of the U shape can be positioned between the two parallel sides and lie perpendicular to the two parallel sides. The third side of the U shape can be the first branch arm 122. The first branch arm 122 can be substantially perpendicular to the plane of the first branch electronics region 124 and the central body 110. The length of the first branch arm 122 can lie substantially parallel to the z-axis. The first branch electronics region 124 and the central body 110 can be spaced at a distance of the length of the first branch arm 122. The third side of the U shape can be approximately the same length as each of the two parallel sides of the U shape.

At block 608, the third branch 160 can be folded at about 90 degrees at the hinge point 166. The hinge point 166 is the point where the third branch arm 162 meets the central body 110. The hinge point 166 is positioned at the distal end of the central body 110 and at the proximal end of the third branch arm 166. As a result, the length of the third branch electronics region 164 can be substantially perpendicular the x-y plane and substantially parallel to the z-axis.

The third branch antenna portion 164BD can lie on the bottom side 100B of the distal end 164BD of the second branch electronics region 144. The third branch 160 can be folded such that the third branch antenna portion 164BD can transmit in a first direction. The third branch antenna portion 164BD can transmit in a first direction substantially parallel to the y-axis. The third branch electronics region 164 can have a length that extends through top level 200 and bottom level 300 of the folded flexible circuit 100. The third branch electronics region 164 can be positioned such that the proximal end 164BP lies on the top level 200 and the distal end 164BD lies on the bottom level 300 of the folded flexible circuit 100.

The final folded configuration of the third branch can create an L shape such that the third branch 160 forms two perpendicular sides. The two sides of the L shape can be the central body 110 and the third branch electronics region 164. The length of the third branch electronics region 164 can be substantially parallel to the z-axis and substantially perpendicular to the x-y plane.

At block 610, the ferrite core 30 can be placed on and secured to the bottom side 100B of the distal end of the third branch electronics region 164BD. The ferrite core 30 can be secured with epoxy or any other adhesive bonding method. As described above, the ferrite core 30 is aligned with the center body portion 110.

At block 612, the fourth branch 180 can be folded at about 90 degrees at the hinge point 186. The hinge point 186 is the point where the fourth branch proximal arm 182 meets the central body 110. The hinge point 186 is positioned at the distal end of the central body 110 and at the proximal end of the fourth branch proximal arm 182. As a result, the length of the fourth branch 180 can be substantially perpendicular the x-y plane as defined above and substantially parallel to the z-axis.

At block 614, the fourth branch 180 can be folded again. The fourth branch 180 can be folded at about 90 degrees at the hinge point 196. The hinge point 196 can be the point where the fourth branch distal arm 188 meets the fourth branch distal electronics region 190. The hinge point 196 can be positioned at the proximal end of the distal electronics region 190 and at the distal end of the fourth branch distal arm 188.

As a result, the fourth branch distal electronics region 190 can lie in plane substantially parallel to the x-y plane. As described above, the central body 110 lies in the x-y plane. Therefore, the fourth branch distal electronics region 190 can lie in a plane parallel to the central body portion 110 and parallel to the first branch electronics region 124. The distance between the fourth branch distal electronics region 190 and the central body portion 110 can be the length of the proximal electronics region 184 and the fourth branch distal arm 188. The distance between the fourth branch distal electronics region 190 and the central body portion 110 can be the length of the ferrite cube 30.

The fourth branch antenna portion 190B can lie on the bottom side 100B of the fourth branch distal electronics region 190B. The fourth branch 180 can be folded such that the fourth branch antenna portion 190B can transmit in a second direction. The fourth branch antenna portion 190B can transmit in a second direction which is substantially orthogonal to the first direction of the antenna portion 164BD and substantially parallel to the z-axis. The fourth branch antenna portion 190B can be positioned at the bottom level 300 of the folded flexible circuit 100.

The final folded configuration of the fourth branch 190 can create a U shape such that the fourth branch 190 forms three perpendicular sides. The three sides of the U shape can be the central body 110, the fourth branch distal electronics region 190, and the combination of the fourth branch proximal electronics region 184 and the fourth branch proximal arm 186. The two parallel sides can be the central body portion 110 and the fourth branch distal electronics region 190. The two parallel sides of the U shape can be approximately equal in length. The fourth branch distal electronics region 190 can lie in a plane substantially parallel to the central body 110. The top side 100A of the central body portion 110A can face the top side 100A of the fourth branch electronics region 190A. The two parallel sides can be approximately equal in length. The third side of the U shape can positioned between the two parallel sides and perpendicular to the two parallel sides. The third side can be the proximal electronics region 184 and the fourth branch distal arm 188. The proximal electronics region 184 and the fourth branch distal arm 188 can be substantially perpendicular to the plane of the fourth branch distal electronics region 190 and to the plane of the central body 100. The lengths of the proximal electronics region 184 and the fourth branch distal arm 188 can lie substantially parallel to the z-axis. The fourth branch distal electronics region 190 and the central body 110 can be spaced at a distance of the lengths of lengths of the proximal electronics region 184 and the fourth branch distal arm 188. The third side of the U shape can be longer in length than the two parallel sides. The third side of the U shape can be approximately twice as long as each of the two parallel sides of the U shape.

The fourth branch distal electronics region 190 can lie in a plane substantially parallel to the central body portion 110. The fourth arm proximal electronics region 184 can lie in a plane substantially perpendicular to the fourth branch distal electronics region 190 and perpendicular to the central body portion 110. The fourth branch proximal electronics region 184 and the fourth branch distal arm 188 can lie substantially parallel to the z-axis. The fourth branch distal electronics region 190 and the central body portion 110 can lie in planes substantially parallel to each other. The fourth branch distal electronics region 190 and the central body portion 110 can be spaced at a distance of the length of the fourth branch proximal electronics region 184 and the fourth branch distal arm 188.

At block 616, the ferrite core 30 can be placed on and secured to the bottom side 100B of the fourth branch distal electronics region 190B. The ferrite core 30 can be secured with epoxy or any other adhesive bonding method. As described above, the ferrite core 30 is aligned with the center body portion 110.

At block 618, the battery or set of batteries 20 can be inserted at the top level 200 of the folded flexible circuit 100. The folded flexible circuit 100 can be folded such that it forms an open cage like structure to receive the battery 20. The battery 20 can be positioned such that it is surrounded by five walls of the open cage like structure: the central body 110, the first branch electronics region 124, the first branch arm 122, the second branch electronics region 144, and the third branch electronics region 164. The open cage like structure may be closed at block 412 when the fourth branch electronic region 190 is folded as discussed more below. The sixth wall of the cage like structure may include the fourth branch proximal electronics region 188 to fully surround the battery 20. The flexible circuit 100 can be folded around the battery 20 as shown in FIGS. 3A-B such that the terminal portions 110B, 124B of the flexible circuit 100 are connected to the positive and negative terminals of the battery 20.

The battery 20 can be a single battery or a combination of multiple batteries. The battery 20 can be wrapped with heat shrink tubing for insulation and protection. The heat shrink tubing can be made of polyester. Hot air can be applied to the heat shrink tubing such that the heat shrink tubing shrinks around the battery 20. The heat shrink tubing can be positioned around the battery 20 such that the negative and positive terminals of the battery 20 are not sealed and can make contact with the terminal portions 110B, 124B of the flexible circuit 100.

The positive terminal portion 110B can lie on the bottom side 100B of the central body 110B. The negative terminal portion 124B can lie on the bottom side 100B of the first branch electronics region 124. The positive and negative terminal portions 110B, 124B can lie parallel to each other and face each other. The terminal portions 110B, 124B can lie in planes substantially perpendicular to the z-axis of the pill. The first branch electronics region 124 can lie in a plane centered between the top and bottom levels 200, 300 of the folded flexible circuit 100 as shown in FIGS. 3A-B. The terminal portions 110B, 124B can lie in planes parallel to each other and spaced at a distance such that the terminal portions 110B, 124B make contact to the corresponding positive and negative ends of the battery 20.

At block 620, the second branch 140 can be folded at about 90 degrees at the hinge point 146. The hinge point 146 is the point where the second branch arm 142 meets the central body 110. The hinge point 146 is positioned at the distal end of the central body 110 and at the proximal end of the second branch arm 142. As a result, the length of the second branch electronics region 144 can be substantially perpendicular the x-y plane and substantially parallel to the z-axis.

The second branch antenna portion 144BD can lie on the bottom side 100B of the distal end 144BD of the second branch electronics region 144. The second branch 140 can be folded such that the second branch antenna portion 144BD can transmit in a third direction substantially perpendicular to the first direction of the third branch antenna portion 164BD and the second direction of the fourth branch antenna portion 190B. The second branch antenna portion 144BD can transmit in a direction substantially parallel to the x-axis.

The second branch electronics region 144 can have a length that extends through top level 200 and bottom level 300 of the folded flexible circuit 100. The second branch electronics region 144 can be positioned such that the proximal end 144BP lies on the top level 200 and the distal end 144BD lies on the bottom level 300 of the folded flexible circuit 100.

The final folded configuration of the second branch 140 can create an L shape such that the second branch 140 forms two perpendicular sides. The two sides of the L shape can be the central body 110 and the second branch electronics region 144. The length of the second branch electronics region 144 can be substantially parallel to the z-axis and substantially perpendicular to the x-y plane.

At block 622, the ferrite core 30 can be placed on and secured to the bottom side 100B of the distal portion of the second branch electronics region 144BD. The ferrite core 30 can be secured with epoxy or any other adhesive bonding method. As described above, the ferrite core 30 is aligned with the center body portion 110.

The final configuration of the folded flexible circuit 100 can be folded such that it forms an open cage like structure to receive the ferrite core 30 as described above. The ferrite core 30 or similar antenna can be positioned at the bottom level 300 of the folded flexible circuit 100. The ferrite core 30 can be positioned such that it is surrounded by the five walls of the open cage like structure: the first branch electronics region 124A, the distal portion of the second electronics region 144BD, the distal portion of the third branch electronics region 164BD, the fourth branch distal arm 188, and the fourth branch distal electronics region 190B. The top side 100A of the first branch electronics region 124A and the bottom side 100B of the three electronics regions (the distal portion of the second electronics region 144BD, the distal portion of the third branch electronics region 164BD, and the fourth branch distal electronics region 190B) can be positioned to all face inward at the bottom level 300 of the folded circuit. The top side 100A of the first branch electronics region 124A and the bottom side 100B of the three electronics regions (the distal portion of the second electronics region 144BD, the distal portion of the third branch electronics region 164BD, and the fourth branch distal electronics region 190B) can be secured to the ferrite core 30, using epoxy or any other adhesive bonding material. The flexible circuit 100 can be folded around the ferrite core 30 as shown in FIGS. 3A-B such that the three antenna portions 144BD, 164BD, 190B are folded and positioned to face outward and to transmit in orthogonal directions.

At block 624, the folded flexible circuit 100 with battery 20 and the ferrite core 30 can be inserted into the pill capsule units 12, 18 as shown in FIG. 3A. The folded flexible circuit 100 with the battery 20 and the ferrite core 30 can be positioned such that the longitudinal axis of the folded flexible circuit 100 can be substantially parallel to the longitudinal axis of the pill 10.

At block 626, the pill capsule units 12, 18 can be closed and secured around the folded flexible circuit 100 with ferrite core 30 and battery 20, as shown in FIG. 4C. The pill capsule 10 can be formed of units 18 and 12 that can be snapped on or secured by any appropriate means to encapsulate the internal electronics of the capsule including the flexible circuit 100, the ferrite core 30 and the battery 20. The pill capsule 10 can be secured using epoxy or any other adhesive bonding method. The curing process can include an ambient cure at room temperature for an extended period of time and an oven cure at an elevated temperature for an extended period of time.

Pill Transmitter

Figure 7:
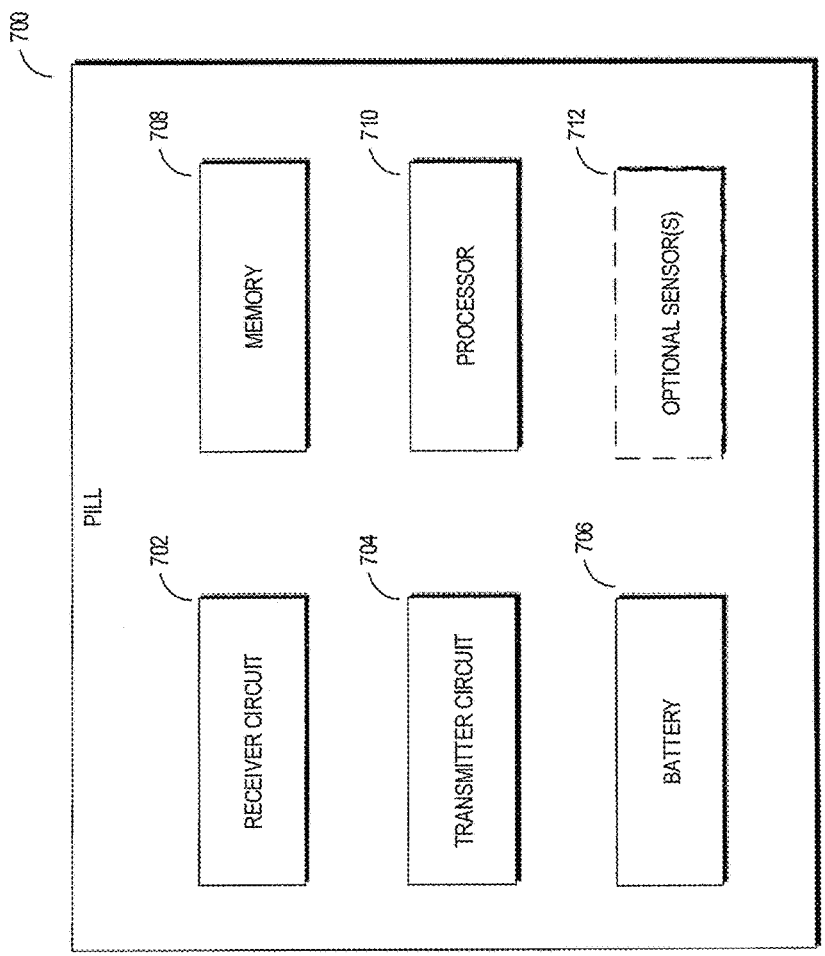

FIG. 7 illustrates an embodiment of a location tracking system of a pill 700 to be swallowed by a patient. An embodiment of the location tracking system of a pill 700 can include the receiver circuit 702, the transmitter circuit 704, the battery 706, the memory 708, the processor 710, and the optional sensors 712. The aspects of the location tracking system of a pill 700 can include programmed instructions capable of being executed on the one or more hardware processors or microcontroller 710. The programmed instructions can be stored in a memory 708. The programmed instructions can correspond to the processes described herein. The engines and other aspects of the processor 710 may also be implemented in a combination of hardware, such as circuits, FPGA, ASICs and the like and programmed instructions. In some embodiments, the processor 710 operates the engines in parallel on the one or more hardware processors.

The processor 710 can control transmission of signals through the transmitter circuit 704. The location tracking system 700 can include memory 708 which can store waveform characteristics like predetermined time intervals and predetermined transmission frequencies. The transmitter circuit 704 can include an antenna for transmitting a signal waveform. In some embodiments, the location tracking system 500 includes multiple transmitting elements or antennas. The location tracking system 500 can also transmit a signal in response to an external trigger signal as discussed more below. The receiver circuit 702 and transmitter circuit 704 may share an antenna. The antenna may be a loop antenna (as discussed more in the above incorporated references). The antenna can wirelessly output or receive wireless communication signals.

The processor 710 can transmit the signals based on a predetermined time interval and at predetermined transmission frequencies. The processor 710 can be programmed to generate pulses that can be emitted from the pill. The processor 710 can be programmed to periodically transmit signals or continuously transmit signals that can be emitted from the pill. In one embodiment, the processor 710 can be programmed to generate three pulses emitted from the pill. Pulse programming can include a selection of pulse frequency of 1 Hz or similar, pulse train definition of 1 or more pulses per transmission window, pulse spacing within the transmission window, pulse amplitude, pulse frequency and pulse durations. In addition to location tracking, the processor 710 can also measure the orientation of the pill. Pulse programming allows the processor 710 to determine the orientation of the pill by the signals at the body antennas 1200.

In some embodiments, pulses can be programmed to uniquely identify a particular capsule and differentiate it from another capsule that might have also been ingested by the patient simultaneously or at some time after the first pill. Any number of pills may be swallowed and tracked simultaneously. Programming could also be used to differentiate one patient from another if one MEU is used in a clinic setting, for example. Programming might also differentiate the intended use of the pill, for example one pulse setting for constipation, one for obstruction, one for gastric emptying studies, or other. In one embodiment, pulses can be uniquely programmed such that timing between the pulses can be differentiated. In some embodiments, where there are three pulses, the time interval between the first pulse and second pulse can be 30 milliseconds and the time interval between the second and third pulse can be 10 milliseconds. This can differentiate the different pulses from a particular pill. In some embodiments, the pill can continuously transmit a signal. other embodiments, the pill can transmit a pulse over a time interval (every 30 milliseconds, every 1 second, every 30 seconds, every 1 minute, every 2 minutes, every 5 minutes, every 30 minutes, every 1 day, etc). Programming can also be used to prevent multiple pills from sending signals simultaneously and causing interference between signals. The individual transmit pulse repetition rates can be set to different carrier radio frequencies, which differentiate between the different pills that are transmitting. The MEU can discriminate the different pill transmissions from the combined mixed signal measurements independent of the pulse rate timing. Algorithms for determining location are described more in detail in application Ser. No. 14/667,563, filed Mar. 30, 2015, titled SYSTEM AND METHOD FOR TRIGGERING A RADIOFREQUENCY TRANSCEIVER IN THE HUMAN BODY hereby incorporated by reference in its entirety.

Initial Pill Activation

The location tracking system of the pill 700 can include a receiver circuit 702 and a transmitter circuit 704. The processor 710 can transmit a signal in response to receiving a trigger signal through the receiver circuit 704. The trigger signal can be transmitted from a stimulator antenna (not shown) or a light source to activate the pill electronics. The processor 710 can activate pill electronics in response to a trigger signal, an external light source, or any applicable external trigger. In an embodiment, a visible light, near infrared light, short wavelength light such as a blue light, or other light can activate a photodiode or photodetector switch, which can turn the electronics on and off for conservation of battery 906. As described above, the photodiode switch 122A can be located on the arm 122 of the flexible circuit 100. In other embodiments, the processor 710 can receive a signal from a magnetic field switch, a pressure activated switch, or some other mechanism to activate the electronic circuits without opening the capsule 10.

Figure 8:
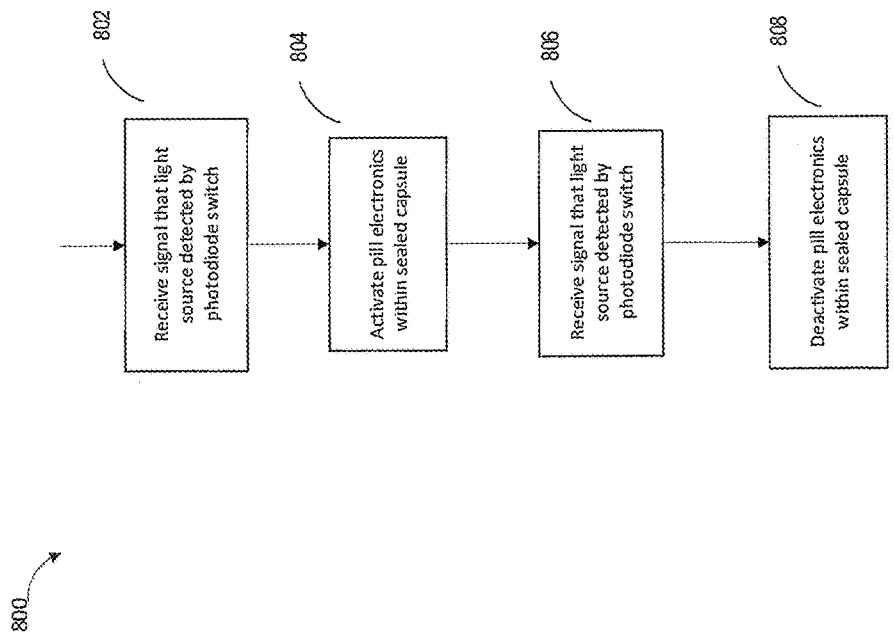
FIG. 8 illustrates an embodiment of a process for activating the pill electronics using a light source.

FIG. 8 illustrates an embodiment of a process 800 for activation of the pill electronics using a light source. In some embodiments, the process 800 can be implemented using the processor 710. In other embodiments, the process 800 can be implemented by a photodiode switch 122A. In some embodiments, the process 800 can be implemented by a magnetic field switch, a pressure activated switch, or some other mechanism to activate the electronic circuits without opening the capsule 10.

At block 802, the processor 710 can receive a signal that a light source has been detected by the photodiode switch 122A. The photodiode switch 122A can be tuned such that it is not activated by normal room level lighting or by sunlight, but can be activated by an intense external visible light source (which could be near infrared as well). The external light source can be a static or pulsed source. In an embodiment, the external light source can be a static source that is slowly swept across the pill circuitry. In an embodiment, the capsule design can use a semi-transparent section of the capsule 10, or a transparent section of the enclosing capsule 10, to allow the switching light to pass through the surface of the capsule 10. In an embodiment, the entire pill capsule 10 can be transparent or semi-transparent. In some embodiments, the pill capsule 10 or semi-transparent sections of the pill capsule 10 can be clear or blue or any other color. At block 804, the processor 710 activates the pill electronics to the on state within the sealed capsule 10. The processor 710 can switch on the power circuitry when the external light source is intentionally illuminated on the photodiode switch 122A.

The circuitry can also be designed to enable the external light source and photodiode switch 122A to turn the electronics off. At block 806, the processor 710 receives a signal that a light source has been detected, similar to block 802. At block 808, the processor 710 activates the photodiode switch 212A again, similar to block 804, to deactivate the pill electronics within the sealed capsule.

In some embodiments, the light source can be internal, rather than external through a transparent outer capsule 10. In some embodiments, the outer capsule 10 of the pill can be partially transparent, transparent, or non-transparent. The capsule electronics can include internal LEDs or other light sources that once activated can activate the photodiode switch 122A.

Instead of a photodiode switch 122A, the circuitry can include a magnetic field switch, a pressure activated switch, or some other mechanism to activate the electronic circuits without opening the capsule 10. In some embodiments, the outer capsule 10 of the pill can be partially transparent, transparent, or non-transparent.

Camera Integration

An example embodiment of a flexible circuit 100 that can be folded to form a three dimensional antenna in a capsule is shown in FIG. 1. The flexible circuit 100 can be partitioned, if necessary, by functional unit. This would enable the circuit to be integrated into another gastrointestinal capsule endoscopy product, or a tethered endoscopy product, or other use, so that the location processing function and capability can be integrated into the other products to add location and tracking data to that product. One example is the parsing of the circuitry and incorporation of that circuitry with a ferrite core 30 or similar antenna into a camera capsule product to enable pictures to be collected of the gastrointestinal system along with the location of the picture.

Figure 9A:
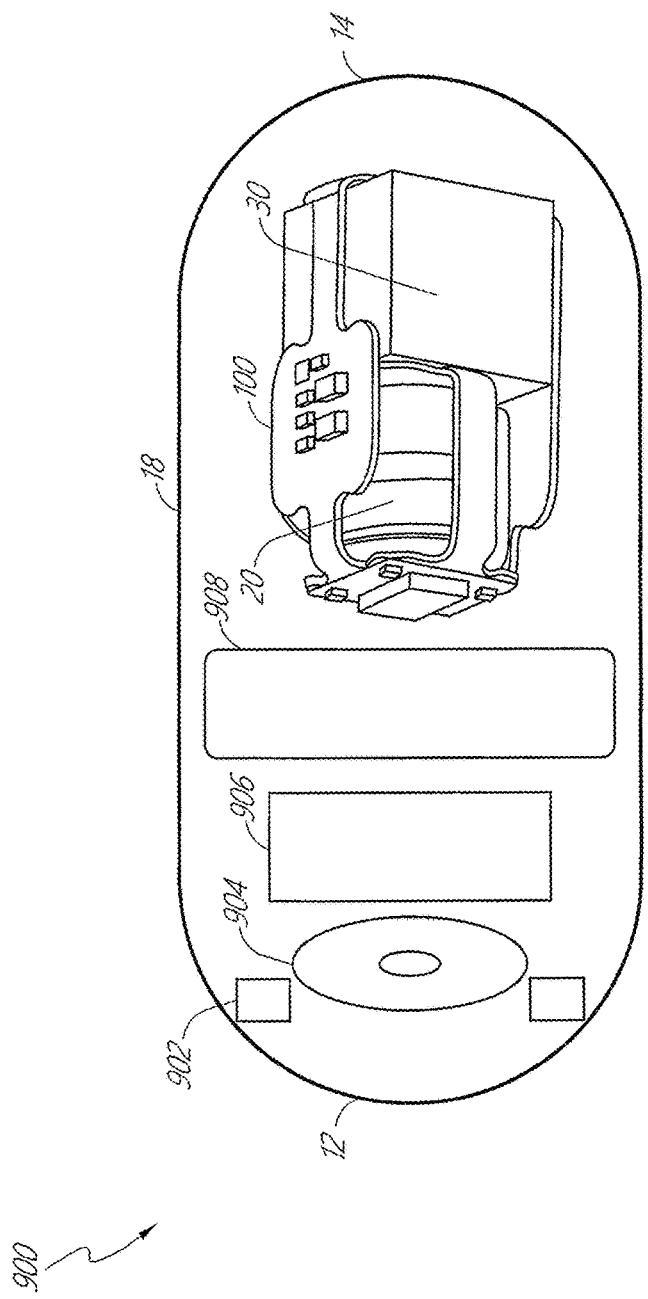
FIGS. 9A-9B illustrate embodiments of a location tracking unit integrated with camera capsule products.
Figure 9B:
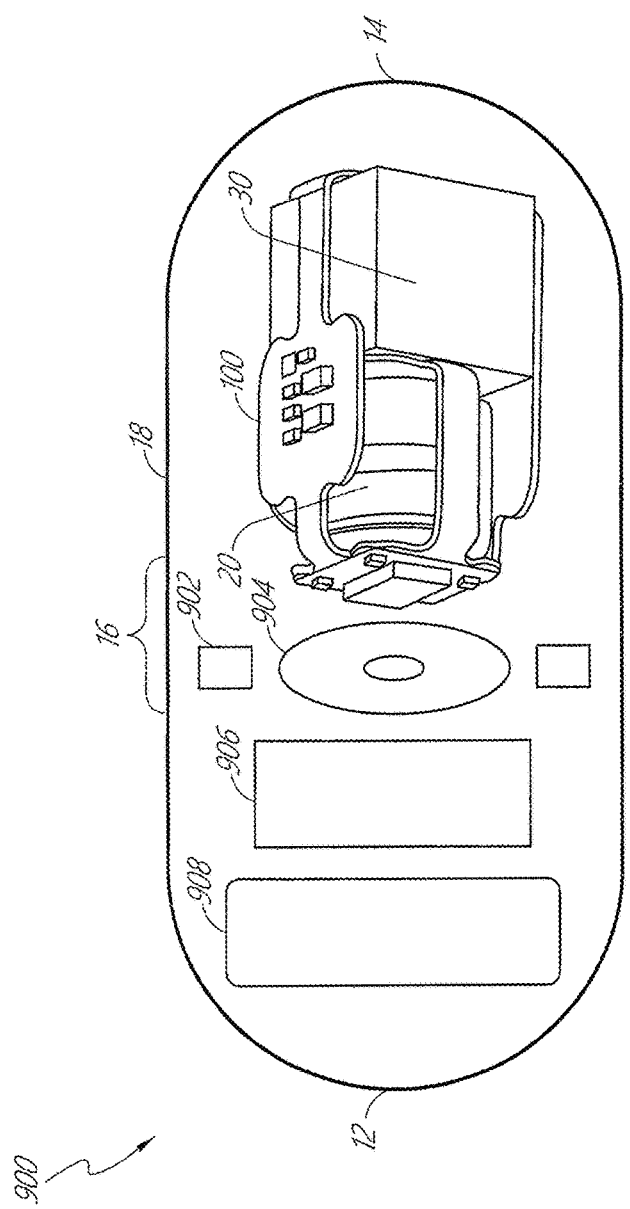

FIGS. 9A-B shows embodiments of a pill capsule 900 integrated with a camera capsule product. The present disclosure can incorporate the flexible circuit 100 with the ferrite core 30 or similar antenna into the camera capsule product. The pill capsule 900 can include a set of optics 904 and a transparent dome 12 on one side of the pill capsule 900. The pill capsule 900 can include the flexible circuit 100 for location tracking on the opposite side of the pill capsule 900. The location tracking unit can include a flexible circuit 100 with the folded antennas portions and ferrite core 30 and batteries 20. The location tracking unit and camera unit can share a set of batteries 20, such that the batteries 20 are centered between the camera capsule unit and the location tracking unit on either side as shown in FIG. 9B. In other embodiments, the camera unit and location tracking unit may each have an independent battery to prolong the battery life of the capsule 900. Similarly, the location tracking unit and camera unit may both be incorporated on a single flexible circuit to minimize the size of the pill capsule. The location tracking unit and camera unit may also have independent circuits for ease of manufacturing, assembly, testing and repair. This would also allow the location tracking unit and camera unit to be independently activated and controlled.

Similarly, the camera unit and location tracking unit may share a switch such as a photodiode switch, a magnetic field switch, a pressure activated switch, or some other mechanism to activate the electronic circuits without opening the pill capsule. In other embodiments, the camera unit and location tracking unit may have independent switches such that each unit can be activated and deactivated independently. Similarly, the camera unit and the location tracking unit can share antenna components or can have independent antenna components.

The camera unit can include optics components 904 such as a lens and lens holder. The camera unit can include light emitting diodes (LEDs) 902 to illuminate the field of vision of the camera to capture images or video of the gastrointestinal system as the pill travels through the patient. The camera unit can also include an image sensor 906. The camera unit can include an integrated circuit transmitter 908 to transmit images or video of the gastrointestinal system to a receiver worn by the patient or placed near the patient. The camera unit can also include an antenna which receives data from the transmitter 908 and sends data to a data recorder.

The outer capsule of the pill 900 can be formed of units 12, 14, 16, 18 that can be snapped on or secured by any appropriate means to encapsulate the internal electronics of the capsule. In some embodiments, one end of the capsule 12 can include a transparent dome on the camera unit side, as shown in FIG. 9A. The transparent dome on the camera unit side would allow the optics 904 to capture images or video of the gastrointestinal tract once the pill 900 is swallowed. In such an embodiment, the other units 18, 16, 14 of the outer capsule of the pill 900 could be non-transparent or transparent.

In some embodiments, the outer capsule of the pill 900 can be formed of units 12, 14, 16, 18. In one embodiment, the outer capsule of the pill 900 can have a transparent dome on both ends units 12, 14 of the outer capsule of the pill 900. The first end unit 12 of the outer capsule can include a transparent dome for the camera unit as discussed above. The other end unit 14 of the outer capsule can also include a transparent dome on the location tracking unit side of the pill 900. The transparent dome on the location tracking unit side of the pill 900 could such that a light source can activate the pill 900 as discussed above. Other embodiments can include camera optics on either side of the pill capsule 900 along the longitudinal axis. The location tracking unit could be located in the center of the pill 900 between the camera optics on either side of the pill 900.

In other embodiments, the other end of the capsule 14 could be non-transparent. The light switch of the location tracking unit could be positioned near the transparent dome on the first end of the capsule 12 such that a light through the transparent dome could reach the photodiode switch to activate the pill electronics. Alternatively, the LEDs 902 of the camera unit could activate the photodiode switch of the location tracking unit.

In another embodiment, the optics 904 can be located in the center of the pill 900 along the longitudinal axis of the pill 900. In this embodiment, the center unit 16 of the outer capsule of the pill 900 along the longitudinal axis of the pill 900 can be transparent to allow the optics 904 to capture images or video the gastrointestinal tract once the pill 900 is swallowed. The transparent section of the outer capsule 900 would similarly allow the photodiode switch to be activated by a light source as discussed above.

The flexible circuit 100 with a ferrite core 30 or similar antenna could also be integrated into an endoscopy and provide the location of the endoscope tip during the endoscopy procedure. Other applications exist as well.

As described above, the orientation of the pill can be tracked as well as the location of the pill. This location and orientation information can be linked to the images and video taken by the camera unit to provide a better understanding of the GI tract.

Connector

Figure 10B:
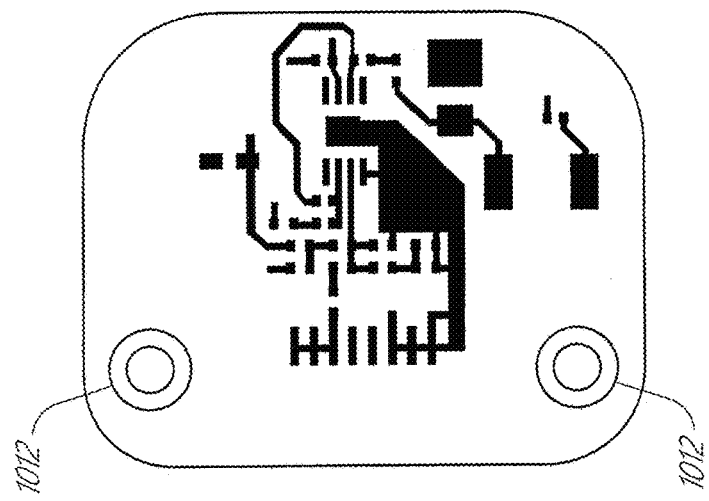
FIGS. 10A-10B illustrate an embodiment of an electrical connector to be connected to the body antenna.
Figure 10A:
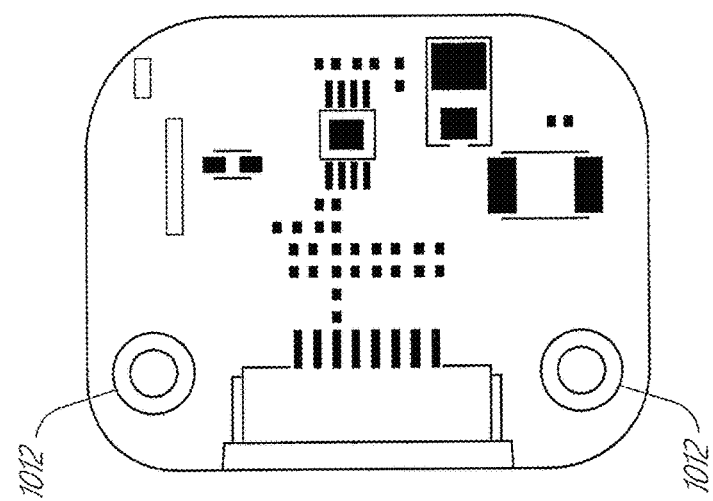
Figure 11A:
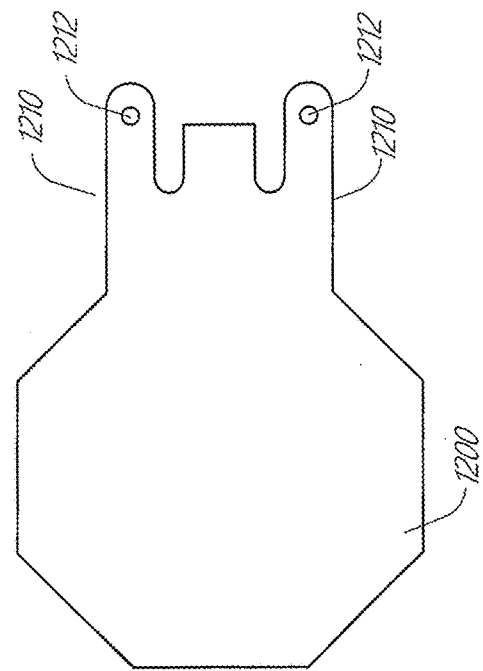
FIG. 11A illustrates an embodiment of a body antenna with the electrical connector installed.

FIGS. 10A-10B illustrate an embodiment of an electrical connector 1000. The electrical connector 1000 can connect to the body antenna 1200 as shown in FIG. 11A. In some embodiments, the design enables the body antenna 1200 to be quickly and securely attached to the cabling, but then easily removable so that the body antenna 1200 can be disposable, but the MEU signal and power cable and connector 1000 can be reused.

Figure 11B:
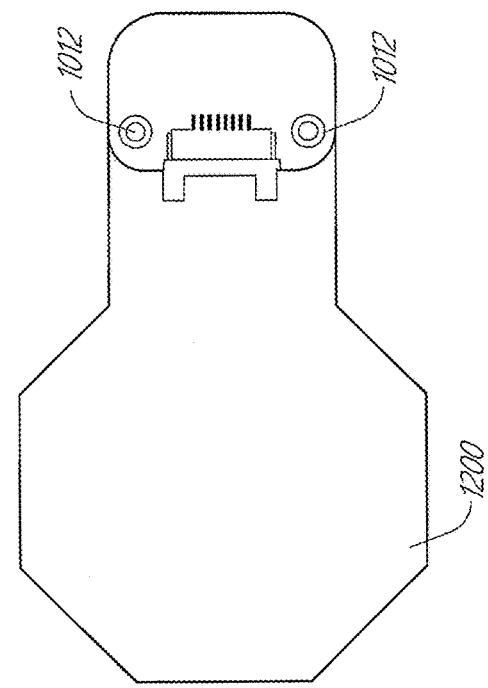
FIG. 11B illustrates the body antenna of FIG. 11A without the components installed, with electrical and mechanical mounting tabs shown.

In some embodiments, the electrical connector 1000 can align with the body antenna tabs 1210 for physical attachment. The electrical connector 1000 can include a fixture that has orthogonal posts made of plastic or other material, to mechanically attach and firmly hold the body antenna 1200. The electrical connector 1000 can include holes 1012 that can align with the holes 1212 of the body antenna tabs 1210 as shown in FIGS. 11A-B. The electrical connector 1000 and the body antenna 1000 can be physically attached. In some embodiments, the physical attachment can be attached by means of a fastener, velcro, glue, any other adhesive, tape, snap fit, screws, or any other appropriate means.

The body antenna 1200 can include physical attachment tabs 1210 which can be designed to easily attach the body antenna 1200 to the electrical connector 1000. The design can enable quick attachment and detachment when in clinical or other use. The body antenna 1200 can include three tabs, two for physical attachment 1210, and one in the center for electrical interfacing 1220. The electrical tab 1210 and mechanical attachment tabs 1210 can use stiffeners to provide a more secure and mechanically robust attachment. The center tab 1020 shown in FIGS. 12A-B can plug into an electrical connector 1000. The electrical connector 1000 interfaces to the MEU electronics signal cable (not shown).

Body Antenna

FIGS. 12A-12B illustrate an embodiment of a body antenna 1200. The body antenna 1200 may also be referred to herein as magnetic or electromagnetic field sensors 1200. The body antenna 1200 can include a tuned antenna coil of one or more wire turns or loop antenna coils 1240 to detect pill magnetic field transmissions. The body antenna 1200 can also include a receiving circuit 1220 which can include signal conditioning and amplification circuits for the detected signals and noise filtering to eliminate unwanted signals. The receiving circuit 1220 can insert to a connector 1000 to interface the circuits to a cable that carries both signal and power.

Figure 13B:
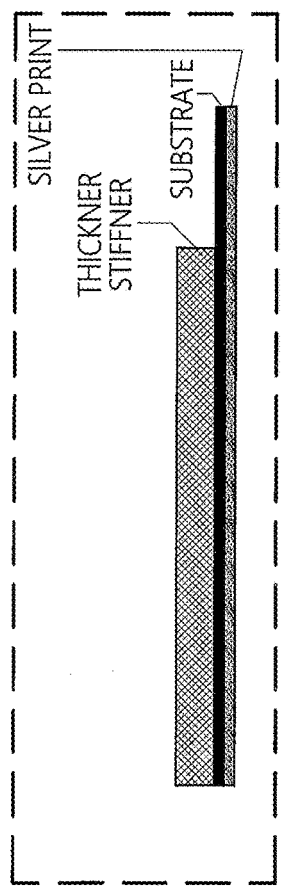
FIGS. 13A-13B illustrate side views of the body antenna circuitry of FIGS. 11A-11B.
Figure 13A:
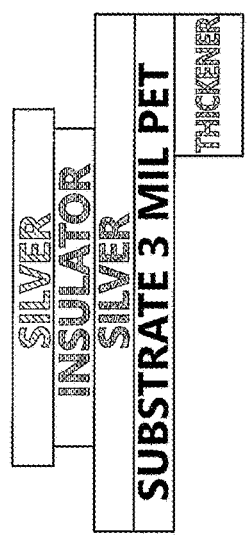

The body antenna 1200 can also include a substrate of plastic, paper, or other materials for these components. The circuit board can have a substrate that is flexible or hard. FIG. 13A illustrates the substrate as a 3 mils polyester material, but a number of different materials of various thicknesses and flexibility can be used as a substrate for the body antenna 1200. The body antenna 1200 can be housed in an encapsulation material such as plastic, paper, or other material, or in an envelope, or other enclosure, that can protect the electronics and the patient when the antenna is attached to or placed near the patient. The body antenna 1200 may include an adhesive, velcro, or other material on one or both sides to attach and secure the antenna directly to a patient's body, or on a shirt, vest, band, or other wearable item.

Multiple body antennas 1200, between 1 to 8 or more, can be attached in a predetermined configuration, potentially on the front, sides, and or back of the patient. These locations can be used as an input by the signal processing system to determine the pill location in the patient. The arrangement may be specific to a particular condition, such as lower intestinal monitoring, or stomach monitoring, or it may be more general for full gastrointestinal system monitoring.

A connector 1000 interfaces the receiving circuit 1220 to a wire set or cable that carries the signals and power. The connector 100 interfacing the body antenna 1200 is shown in FIG. 11A. The body antenna cable can connect to the MEU for signal analysis and processing of pill location, as discussed more in the above incorporated references. In some embodiments, the signal analysis and processing can be performed by an external computing system and the signals from MEU can be wirelessly transmitted to the external computing system.

As illustrated, the body antenna 1200 can include an octagonal region for placement of the receiving coils or body antenna coils 1240. Although the body antenna 1200 is illustrated with an octagonal region, the region could also be round, or square, or another shape. The octagonal region can provide ease of manufacturing and printing over round regions as traditional printing and manufacturing methods can have difficulty with curved placements. In another embodiment, the region can be circular to increase the surface area and therefore increase the signal. In other embodiments, the region can be round which can increase the surface area for improved signal. In one embodiment, the body antenna 1200 includes an extension off the edge of the octagon region that includes the receiving circuit 1220 as well as physical attachment tabs 1210. FIG. 12B illustrates an enlarged view of the receiving circuit 1220 of the body antenna 1200 which can be inserted into the electronic connector 1000.

The receiving coils 1240 can include of one or more wraps of conductor around the perimeter of the flexible circuit octagon. The receiving coils 1240 can be electrically tuned and filtered to be a component in the body antenna circuit to optimize its frequency response to the capsule antenna emissions and reduce noise and interference as much as possible.

In some embodiments, the receiving coils 1240 can be printed on a flexible circuit board. FIG. 13A illustrates a side view of the circuitry of the body antenna 1200. In some embodiments, a substrate can be first placed to act as a base for further printing. In some embodiments, a bridge 1230 can be used to connect the wraps of conductor 1240 to the receiving circuit 1220. The bridge 1230 can include insulator that can be placed between layers of conductive ink, such as silver ink as shown in FIG. 13A. The use of the bridge 1230 can help ease of manufacturing and printing. During manufacturing, the printer can print several wraps of conductor 1240 around the perimeter of the body antenna 1200. The initial point of printing can connect to the receiving circuit 1220. The printer may then print several wraps of conductor 1240 around the perimeter of the body antenna 1200. At the end of printing, the final point of connection to the receiving circuit 1220 may be placed on the bridge 1230 such that there is proper flow of current through the circuit. This minimizes fabrication steps to lower production cost and complexity.

The body antenna 1200 can include physical attachment tabs 1210 which can be designed to easily attach the body antenna 1200 to the cable assembly, enabling quick attachment and detachment from the electrical connector 1000 when in clinical or other use. The tab configuration of the body antenna 1000 can include three tabs, two for physical attachment 1210, and an electrical tab 1220 in the center for electrical signal interfacing. This center electrical tab 1220 can include the receiving circuit 1220 which can plug into an electrical signal connector 1000 that interfaces to the MEU electronics signal cable. The electrical tab 1220 and physical attachment tabs 1210 can use stiffeners to provide a more secure and mechanically robust attachment as shown in FIG. 13B.

In some embodiments, the body antenna coil 1240, the receiving circuit 1220 and MEU electronics signal cable can be integrated into a single component, such that there is no need for inclusion of the bridge 1230 or the electrical connector 1000. This can provide ease of manufacturing and lower cost.

Additional Embodiments

Any of the embodiments described above may be modified or added to as follows.

The magnetic dipole antennas described herein can be used as the transmitting or receiving antennas in a pill transponder capsule designed for gastrointestinal disorder diagnostics or clinical testing. A three dimensional antenna array can enable signals from the capsule to be optimally detected by receiving antennas placed on a patient's body, typically the chest, abdomen, and back. The signal detection, by virtue of the dipole antenna array, can be substantially less sensitive to capsule orientation than it would be with a simple dipole arrangement.

The antennas can be miniature in size for use in a gastrointestinal motility monitoring capsule. The antennas would be wrapped as coils around a cube of ferrite material, with the cube size being on the order of 5 mm on a side. This small size enables the overall capsule to be easily swallowed by adults, children, and the elderly, yet highly efficient in its ability to transmit a signal to receivers outside the body.

A two dimensional dipole antenna array can enable signal direction control for a planar application, such as a system including the array to be on a table, floor, or other flat surface.

The antennas, in two or three dimensional configurations, can be utilized by systems such as RFID tags on products, inventory, or industrial applications to improve RFID signal reception by such systems.

The antennas can be used in systems or devices that transmit in the traditional AM radio, FM radio, RFID, or other low frequency or signal communications bands that range from 1 kHz to over 100 MHz.

The antennas can be used in systems or devices that transmit in the traditional cellular phone communications bands to improve handset reception by removing the directionality of digital and analog data from cellular systems.

The antennas can be used in inductively coupled charging systems, such as in cellular phones, handheld equipment, and other instrumentation, in order to improve coupling effectiveness when the instrument charging circuitry is not optimally aligned with the inductive coupling charging system.

The antennas can be embedded into the pill capsule walls or adhered to the inside of the pill capsule.

The pill capsule can include a compartment for a drug or treatment. The pill capsule can include a membrane for drug elution or other mechanism for drug release. As the location of the capsule is tracked through the body, the processor of the pill can trigger the elution of the drug at a particular location of the GI tract for targeted treatment.

The pill capsule electronics can include cameras, chemical sensors, pH meters, pressure sensors, flow sensors, and other sensors to measure and study the GI tract once the pill is ingested.

The pill capsule electronics can include a light emitting diode (LED), laser diode (LD), or UV diode that could be used to irradiate a specific target along the GI tract. For example, the LED, LD, UV diode can target a specific section of the bowel to kill surface bacteria for therapeutic or antiseptic treatment. For example, the LED or LD light source can make photochemical changes to the inner surface of the lumen of the GI tract. For example, the LED, LD, or UV diode can be applied to lesions or polyps within the GI tract.

The pill capsule can exclude the ferrite core. The folded flexible circuit can be produced and inserted into a pill capsule without the ferrite core. In some embodiments, the pill capsule can instead include a mechanical structure made of plastic or any other suitable material to maintain the structure of the folded flexible circuit.

Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated.

Furthermore, it should be understood when referring to direction of magnetic field or signals, it does not necessarily mean that there is no magnetic field outside of the axis of transmission. Thus, when direction of magnetic the field is discussed with respect to transmitting elements, it may be in relation to where a receiving element may experience highest magnetic field.

The term "substantially parallel," when used to describe two axes or planes, in addition to having its ordinary meaning, may refer to an angle between a first and a second axis (or plane) that is 0 degrees, less than or equal to 1 degree, a few degrees, or less than or equal to some other small value, such as 10 or 15 degrees. Furthermore, the terms "substantially orthogonal" or "substantially perpendicular," when used to describe two axes or planes, in addition to having their ordinary meaning, may refer to an angle between a first and a second axis (or plane) that is 90 degrees or that is between 75 and 105 degrees, that is between 80 and 100 degrees, that is between 85 and 95 degrees, that is between 89 and 91 degrees, or that is otherwise close to 90 degrees or within some small variance from 90 degrees.

The terms "recess," "receptacle," "cavity," or "cage-like structure," in addition to having their ordinary meanings, may refer to an area, space, or void fully enclosed, partially enclosed, or surrounded by a structure such that a component can be inserted or placed within the area, space, or void.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, a smartphone, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, terms such as "above," "below," "top," and "bottom" are used throughout the specification. These terms should not be construed as limiting. Rather, these terms are used relative to the orientations of the applicable figures.

What is claimed is:

1. A flexible circuit configured to be inserted into a pill capsule, the flexible circuit comprising:
    a first portion comprising an electrical contact configured to electrically connect with a first terminal of a battery;
    a second portion having an electrical contact configured to electrically connect with a second terminal of the battery;
    a first arm having a length separating the first portion and the second portion;
    a third portion comprising a first antenna;
    a second arm having a length separating the first portion and the third portion;
    a fourth portion comprising a second antenna;
    a third arm having a length separating the first portion and the fourth portion;
    a fifth portion comprising a third antenna;
    wherein the first portion, the second portion, and first arm are configured to form a first receptacle in a folded configuration;
    wherein the first receptacle is configured to receive the battery;
    wherein the third portion, the fourth portion, and the fifth portion are configured to form a second receptacle in the folded configuration; and
    wherein the second receptacle is configured to receive a cube ferrite core.

2. The flexible circuit of claim 1, wherein the first portion is positioned substantially parallel to the second portion in the folded configuration, wherein the fifth portion is positioned substantially parallel to the first portion and the second portion in the folded configuration.

3. The flexible circuit of claim 1, wherein the third portion is positioned substantially perpendicular to the fourth portion in the folded configuration, wherein the fifth portion is positioned substantially perpendicular to the third portion and the fourth portion in the folded configuration.

4. The flexible circuit of claim 1, wherein the first antenna is configured to transmit a first transmit signal in a first direction, wherein the second antenna is configured to transmit a second transmit signal in a second direction, wherein the third antenna is configured to transmit a third transmit signal in a third direction, wherein the first direction is substantially perpendicular to the second direction and the third direction, wherein the second direction is substantially perpendicular to the first direction and third direction, and wherein the third direction is substantially perpendicular to the first direction and the second direction.

5. The flexible circuit of claim 1, wherein the first receptacle has a volume proportional to the length of the first arm.

6. The flexible circuit of claim 1, further comprising the battery positioned in the first receptacle.

7. The flexible circuit of claim 1, further comprising the ferrite core positioned in the second receptacle.

8. The flexible circuit of claim 1, wherein the flexible circuit is integrated with a camera unit.

9. The flexible circuit of claim 1, further comprising a photodiode switch configured to detect optical radiation and activate operation of an electrical component in response to the detected optical radiation, wherein the photodiode switch is positioned on.

10. A flexible circuit configured to be inserted in a pill capsule, the flexible circuit body comprising:
a base;
a first arm extending from the base, the first arm configured to fold on a first side of the base;
a second arm extending from the base, the second arm configured to fold on a second side opposite from the first side;
wherein the base, the first arm, and the second arm are configured to form a first recess and a second recess in a folded configuration; and
wherein the first recess is configured to house a battery and the second recess is configured to house a ferrite core.

11. The flexible circuit of claim 10, wherein a length of the first arm is substantially equal to a sum of a length of the battery and a length of the ferrite core.

12. The flexible circuit of claim 10, wherein a first volume of the battery is substantially equal to the first recess and a second volume ferrite core is substantially equal to the second recess, thereby reducing empty space.

13. The flexible circuit of claim 10, wherein an empty volume defined by a difference between a volume formed by the base, the first arm, and the second arm and a volume of the battery and a volume of the ferrite core is less than 20%.

14. The flexible circuit of claim 10, wherein the first arm is positioned substantially parallel to the second arm.

15. The flexible circuit of claim 10, further comprising the battery positioned in the first recess.

16. The flexible circuit of claim 10, further comprising the ferrite core positioned in the second recess.

* * * * *